US010993667B2

(12) United States Patent
Lowery

(10) Patent No.: US 10,993,667 B2
(45) Date of Patent: May 4, 2021

(54) METHOD AND APPARATUS FOR APPLYING A TRACING TO AN EXPANDABLE DEVICE

(71) Applicant: ECOM Medical, Inc., San Juan Capistrano, CA (US)

(72) Inventor: Guy Russell Lowery, San Juan Capistrano, CA (US)

(73) Assignee: ECOM Medical, Inc., San Juan Capistrano, CA (US)

(*) Notice: Subject to any disclaimer, the term of this patent is extended or adjusted under 35 U.S.C. 154(b) by 0 days.

(21) Appl. No.: 16/370,969

(22) Filed: Mar. 30, 2019

(65) Prior Publication Data
US 2019/0320983 A1 Oct. 24, 2019

Related U.S. Application Data

(63) Continuation of application No. 15/571,350, filed as application No. PCT/US2016/031356 on May 6, 2016, now abandoned.
(Continued)

(51) Int. Cl.
*B05D 1/32* (2006.01)
*B05B 12/20* (2018.01)
(Continued)

(52) U.S. Cl.
CPC .............. *A61B 5/6853* (2013.01); *A61B 5/02* (2013.01); *A61B 5/02444* (2013.01);
(Continued)

(58) Field of Classification Search
None
See application file for complete search history.

(56) References Cited

U.S. PATENT DOCUMENTS 3,535,758 A * 10/1970 Hoet .................. H01J 19/00
445/49
4,062,104 A * 12/1977 Carlsen .................. G01K 7/04
29/592.1
(Continued)

FOREIGN PATENT DOCUMENTS

GB 1467344 3/1977
JP H06-072658 U 10/1994
(Continued)

OTHER PUBLICATIONS

"Cardiac Output from an Endotracheal Tube. What Could be Easier?" CONMED Corporation brochure. Sep. 2008.
(Continued)

*Primary Examiner* — Cachet I Proctor
(74) *Attorney, Agent, or Firm* — Blair Walker IP Services, LLC

(57) ABSTRACT

A system for obtaining signals related to electrical activity of the heart of a subject includes a sensing device including an elongate member having a distal end configured for placement within a body lumen of a subject, and a proximal end configured to extend from the subject, an actuation portion carried by the elongate member and configured for placement within the body lumen, the actuation portion having a low-profile state for delivery within the body lumen and an expanded state, and one or more sensors disposed on the actuation portion, each including a contact surface configured to contact an interior wall of the body lumen, wherein the actuation portion is configured to cause the contact surface of each of the one or more sensors to contact a location on the interior wall of the body lumen to provide a signal component for producing one or more electrocardiogram signals.

22 Claims, 21 Drawing Sheets

Related U.S. Application Data

(60) Provisional application No. 62/158,504, filed on May 7, 2015, provisional application No. 62/159,912, filed on May 11, 2015.

(51) Int. Cl.

| | | |
|---|---|---|
| *A61B 5/02* | (2006.01) | |
| *A61B 5/00* | (2006.01) | |
| *A61B 5/024* | (2006.01) | |
| *A61B 5/285* | (2021.01) | |
| *A61B 5/287* | (2021.01) | |
| *A61M 16/04* | (2006.01) | |
| *A61B 17/00* | (2006.01) | |
| *H05K 3/14* | (2006.01) | |

(52) U.S. Cl.
CPC .............. *A61B 5/285* (2021.01); *A61B 5/287* (2021.01); *A61B 5/6819* (2013.01); *A61B 5/6858* (2013.01); *A61M 16/0434* (2013.01); *A61B 2017/00044* (2013.01); *A61B 2562/0209* (2013.01); *A61B 2562/125* (2013.01); *A61M 2230/04* (2013.01); *H05K 3/14* (2013.01)

(56) References Cited

U.S. PATENT DOCUMENTS

| | | |
|---|---|---|
| 4,304,239 A | 12/1981 | Perlin |
| 4,351,330 A | 9/1982 | Scarberry |
| 4,383,534 A | 5/1983 | Peters |
| 4,640,298 A | 2/1987 | Pless et al. |
| 4,706,688 A | 11/1987 | Don Michael et al. |
| 4,817,611 A | 4/1989 | Arzbaecher et al. |
| 4,836,214 A | 6/1989 | Sramek |
| 4,852,580 A | 8/1989 | Wood |
| 5,005,573 A | 4/1991 | Buchanan |
| 5,010,888 A | 4/1991 | Jadvar et al. |
| 5,024,228 A | 6/1991 | Goldstone et al. |
| 5,056,532 A | 10/1991 | Hull et al. |
| 5,069,215 A | 12/1991 | Jadvar et al. |
| 5,129,396 A | 6/1992 | Rosen et al. |
| 5,179,952 A | 1/1993 | Buinevicius et al. |
| 5,343,860 A | 9/1994 | Metzger et al. |
| 5,379,765 A | 1/1995 | Kajiwara et al. |
| 5,682,880 A | 11/1997 | Brain |
| 5,782,774 A | 7/1998 | Shmulewitz |
| 5,791,349 A | 8/1998 | Shmulewitz |
| 6,061,134 A | 5/2000 | Jensen et al. |
| 6,095,987 A | 8/2000 | Shmulewitz |
| 6,292,689 B1 | 9/2001 | Wallace et al. |
| 6,517,492 B2 | 2/2003 | Koblanski |
| 6,584,343 B1 | 6/2003 | Ransbury et al. |
| 7,220,230 B2 | 5/2007 | Roteliuk et al. |
| 7,229,437 B2 | 6/2007 | Johnson et al. |
| 7,234,225 B2 | 6/2007 | Johnson et al. |
| 7,867,547 B2 | 1/2011 | Tochterman et al. |
| 7,879,387 B2 | 2/2011 | Myers |
| 8,273,053 B2 | 9/2012 | Saltzstein |
| 8,371,241 B2 | 2/2013 | Sedberry et al. |
| 8,634,894 B2 | 1/2014 | Rea et al. |
| 8,805,466 B2 | 8/2014 | Salahieh et al. |
| 9,028,472 B2 | 5/2015 | Mathur et al. |
| 9,037,226 B2 | 5/2015 | Hacker et al. |
| 9,289,141 B2 | 3/2016 | Lowery et al. |
| 9,415,416 B2 | 8/2016 | Pacetti et al. |
| 9,486,145 B2 | 11/2016 | Feer et al. |
| 9,579,152 B2 | 2/2017 | Prakash et al. |
| 9,707,034 B2 | 7/2017 | Shaer |
| 2003/0176816 A1 | 9/2003 | Maguire et al. |
| 2005/0065586 A1 | 3/2005 | Johnson |
| 2005/0158449 A1 | 7/2005 | Chappa |
| 2005/0210672 A1* | 9/2005 | Reynolds ................ G02F 1/155 29/830 |
| 2006/0029720 A1 | 2/2006 | Panos et al. |
| 2006/0162730 A1 | 7/2006 | Glassenberg et al. |
| 2007/0005052 A1 | 1/2007 | Kampa |
| 2007/0083192 A1 | 4/2007 | Welch |
| 2007/0260133 A1 | 11/2007 | Meyer |
| 2009/0062666 A1 | 3/2009 | Roteliuk |
| 2009/0062771 A1 | 3/2009 | Tarola et al. |
| 2009/0192381 A1 | 7/2009 | Brockway et al. |
| 2009/0227885 A1* | 9/2009 | Lowery .................. A61B 5/029 600/526 |
| 2010/0055294 A1 | 3/2010 | Wang et al. |
| 2011/0072659 A1 | 3/2011 | Swanson et al. |
| 2011/0137155 A1 | 6/2011 | Weber et al. |
| 2011/0213338 A1 | 9/2011 | Paskar |
| 2012/0130363 A1 | 5/2012 | Kim et al. |
| 2012/0138460 A1 | 6/2012 | Baghbani-Parizi et al. |
| 2012/0215074 A1 | 8/2012 | Krimsky |
| 2013/0085416 A1 | 4/2013 | Mest |
| 2013/0144145 A1 | 6/2013 | Meng |
| 2013/0338480 A1 | 12/2013 | Hann |
| 2014/0228838 A1 | 8/2014 | Kirschenman |
| 2014/0243821 A1* | 8/2014 | Salahieh .................. A61N 1/05 606/41 |
| 2014/0257068 A1 | 9/2014 | Anderson et al. |
| 2014/0257281 A1 | 9/2014 | Squire et al. |
| 2014/0296823 A1 | 10/2014 | Ward et al. |
| 2015/0004208 A1 | 1/2015 | Monjo Cabrer et al. |
| 2015/0005764 A1 | 1/2015 | Hanson et al. |
| 2015/0025532 A1* | 1/2015 | Hanson .............. A61B 18/1492 606/41 |
| 2015/0025533 A1 | 1/2015 | Groff et al. |
| 2015/0112172 A1 | 4/2015 | Atlee et al. |
| 2015/0173773 A1 | 6/2015 | Bowman et al. |
| 2015/0165301 A1 | 7/2015 | Smith et al. |
| 2015/0265440 A1 | 9/2015 | Maruyama et al. |
| 2015/0366508 A1 | 12/2015 | Chou et al. |
| 2015/0366608 A1 | 12/2015 | Weber et al. |
| 2016/0129223 A1 | 5/2016 | Kirschenman |
| 2016/0287278 A1 | 10/2016 | Stigall et al. |
| 2016/0296744 A1 | 10/2016 | Chen et al. |
| 2016/0338647 A1 | 11/2016 | Sterrett et al. |
| 2016/0345857 A1 | 12/2016 | Jensrud et al. |
| 2017/0231572 A1 | 8/2017 | Lowery |

FOREIGN PATENT DOCUMENTS

| | | |
|---|---|---|
| WO | WO2014168987 A1 | 10/2014 |
| WO | WO2016094938 A9 | 6/2016 |

OTHER PUBLICATIONS

Campos, J., "Double-Lumen Endotracheal Tubes," downloaded May 4, 2016 https://www.scahq.org/sca3/events/2009/annual/syllabus/workshops/subs/wkshp1pdfs/Double%20Lumen%20Tubes%20-%20Campos.doc.pdf.

PCT International Search Report and Written Opinion for PCT/US2016/031356, ECOM Medical, Inc., Forms PCT/ISA/220, 210, and 237 dated Aug. 8, 2016 (14 pages).

Extended European Search Report dated Mar. 19, 2018, in EP App. No. 16790208.9 filed May 6, 2016 (7 pages).

Extended European Search Report dated Oct. 8, 2020, in EP App. No. 20173911.7 (8 pages).

* cited by examiner

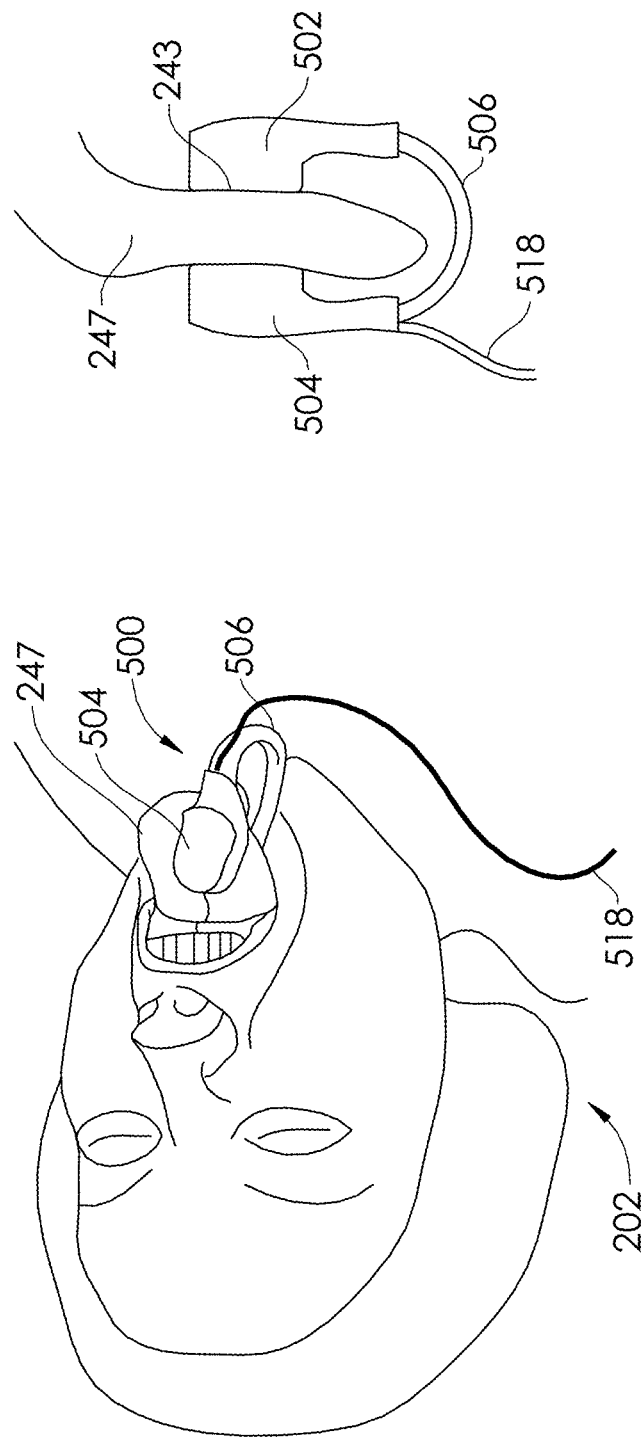

METHOD AND APPARATUS FOR APPLYING A TRACING TO AN EXPANDABLE DEVICE

INCORPORATION BY REFERENCE TO ANY PRIORITY APPLICATIONS

This application is a continuation of U.S. patent application Ser. No. 15/571,350, filed on Nov. 2, 2017, now abandoned, which is a U.S. National Stage patent application for PCT application no. PCT/US2016/031356, filed on May 6, 2016, which claims the benefit of priority to U.S. Provisional Application No. 62/158,504, filed on May 7, 2015, and to U.S. Provisional Application No. 62/159,912, filed on May 11, 2015, all of which are incorporated by reference in their entirety herein for all purposes. Priority is claimed pursuant to 35 U.S.C. § 120 and 35 U.S.C. § 119.

FIELD OF THE INVENTION

The field of the invention generally relates to systems for sensing electrical activity of the heart, at least partially from naturally-occurring internal body surfaces.

BACKGROUND

Currently human electrocardiogram (ECG) signals are acquired by placing three to ten electrode pads on the external body surface using adhesive pads that can be connected to electrical wires. For example 3, 5, 7, 9, or 10 electrode pads may be placed. The "12 lead" ECG actually uses 10 electrodes (one generally serves as a ground), with some of the leads being bipolar and some monopolar, thus producing twelve different ECG vectors. The method involves a driven ground and a program/electronic circuit designed to acquire the electrical signals associated with the functioning of the heart. This signal is comprised of the PQRST waveform for each heartbeat. The PQRST waveform generally includes a QRS complex, which can be associated with the depolarization of the ventricles of the heart. Clinicians can look at the signals and diagnose cardiac functionality and timing important for patient management. The multiple electrode pads, which are commonly located on the arms, legs, feet, shoulders, chest, and other areas, can interfere with diagnostic and therapeutic procedures. The electrode pads may also be damaged by diagnostic and therapeutic procedures. In some patients, including, but not limited to burn or other trauma patients, sufficient skin areas may not be available for placement of the electrode pads. In coupling to the skin the electrode pads include a coupling gel, whose properties can change with time, sometimes causing the electrode pads to malfunction or fall off. The difficulties with placement of the electrode pads may delay the obtainment of the ECG. This can be a critical occurrence in patients having urgent needs.

SUMMARY OF THE INVENTION

In one embodiment of the present invention, a system for obtaining signals related to electrical activity of the heart of a subject includes a sensing device including an elongate member having a proximal end and a distal end, the distal end configured for placement within a body lumen of a subject, the proximal end configured to extend from the subject, an actuation portion carried by the elongate member and configured for placement within the body lumen of the subject, the actuation portion having a low-profile state for delivery within the body lumen of the subject and an expanded state, and one or more sensors disposed on the actuation portion, each of the one or more sensors including a contact surface configured to contact an interior wall of the body lumen, wherein the actuation portion is configured to cause the contact surface of each of the one or more sensors to contact a location on the interior wall of the body lumen to provide a signal component for producing one or more electrocardiogram signals.

In another embodiment of the present invention, a method for obtaining signals related to electrical activity of the heart of a subject includes providing a sensing device including an elongate member having a proximal end and a distal end, the distal end configured for placement within a body lumen of a subject, the proximal end configured to extend from the subject, an actuation portion carried by the elongate member and configured for placement within the body lumen of the subject, the actuation portion having a low-profile state for delivery within the body lumen of the subject and an expanded state, and one or more sensors disposed on the actuation portion, each of the one or more sensors including a contact surface configured to contact an interior wall of the body lumen, wherein the actuation portion is configured to cause the contact surface of each of the one or more sensors to contact a location on the interior wall of the body lumen to provide a signal component for producing one or more electrocardiogram signals, inserting the sensing device in or near its low-profile state into a body cavity or body lumen of a subject, causing the actuation portion of the sensing device to move from its low-profile state towards its expanded state such that the contact surface of each of the one or more sensors contacts an interior surface of the body cavity of body lumen of the subject, and obtaining one or more electrocardiogram signals from the sensing device.

In another embodiment of the present invention, a method for obtaining signals related to electrical activity of the heart of a subject includes providing a sensing device including an elongate member having a proximal end and a distal end, the distal end configured for placement within a body lumen of a subject, the proximal end configured to extend from the subject, an actuation portion carried by the elongate member and configured for placement within the body lumen of the subject, the actuation portion having a low-profile state for delivery within the body lumen of the subject and an expanded state, and one or more sensors disposed on the actuation portion, each of the one or more sensors including a contact surface configured to contact an interior wall of the body lumen, wherein the actuation portion is configured to cause the contact surface of each of the one or more sensors to contact a location on the interior wall of the body lumen to provide a signal component for producing one or more electrocardiogram signals, wherein the one or more sensors of the actuation portion of the sensing device includes two or more electrodes, providing at least one auxiliary sensor having a contact surface configured to couple to a portion of the subject remote from the interior of the body lumen, providing at least one external sensor configured to be coupled to the skin with coupling gel or coupling liquid, inserting the sensing device in or near its low-profile state into a body cavity or body lumen of a subject, causing the actuation portion of the sensing device to move from its low-profile state towards its expanded state such that the two or more electrodes contact an interior surface of the body cavity of body lumen of the subject, coupling the contact surface of the at least one auxiliary sensor to mucosa of the subject, coupling an electrode of the at least one external sensor to a portion of the skin of the subject, and obtaining one or more electrocardiogram signals from each of the sensing device, the at least one auxiliary sensor, and the at least one external sensor.

In yet another embodiment of the present invention, an apparatus for applying a tracing to an inflatable device includes a body having a cavity extending longitudinally within and a wall, one or more longitudinally extending openings in the wall and opening into the cavity, such that an inflatable device placed within the cavity it partially covered by the wall and partially uncovered by the one or more openings, and wherein the one or more openings are configured to allow the application of a conductive material to a portion of the inflatable device that is uncovered while blocking the application of the conductive material to a portion of the inflatable device that is covered by the wall.

In still another embodiment of the present invention a method for applying a conductive tracing to an inflatable device includes placing an inflatable device within a body having a cavity extending longitudinally within and a wall, the body including one or more longitudinally extending openings in the wall and opening into the cavity such that the inflatable device placed within the cavity is partially covered by the wall and partially uncovered by the one or more openings, applying a conductive material to a portion of the inflatable device, and when the conductive material is in a condition that will not significantly change upon removal of the inflatable device from the body, removing the inflatable device from the body.

In yet another embodiment of the present invention an apparatus for applying a tracing to an inflatable device includes a body having a cavity extending longitudinally within and a wall, one or more longitudinally extending openings in the wall and opening into the cavity, such that an inflatable device placed within the cavity it partially covered by the wall and partially uncovered by the one or more openings, and wherein the one or more openings are configured to allow the application of a material to a portion of the inflatable device that is uncovered while blocking the application of the conductive material to a portion of the inflatable device that is covered by the wall, wherein the material is configured to be applied in a flowable state and changeable to a non-flowable or substantially non-flowable state.

In still another embodiment of the present invention a sensing device for obtaining signals related to electrical activity of the heart of a subject, the sensing device produced by the method including placing an expandable device within a body having a cavity extending longitudinally within and a wall, the body including one or more longitudinally extending openings in the wall and opening into the cavity such that the expandable device placed within the cavity is partially covered by the wall and partially uncovered by the one or more openings, applying a conductive material to a portion of the expandable device, and when the conductive material is in a condition that will not significantly change upon removal of the expandable device from the body, removing the expandable device from the body.

BRIEF DESCRIPTION OF THE DRAWINGS

FIG. 21 is a perspective view of a subject having an auxiliary sensor placed on a portion of the tongue.

FIG. 22 is a sectional view of the auxiliary sensor in place on the subject's tongue.

DETAILED DESCRIPTION OF THE ILLUSTRATED EMBODIMENTS

Figure 1:
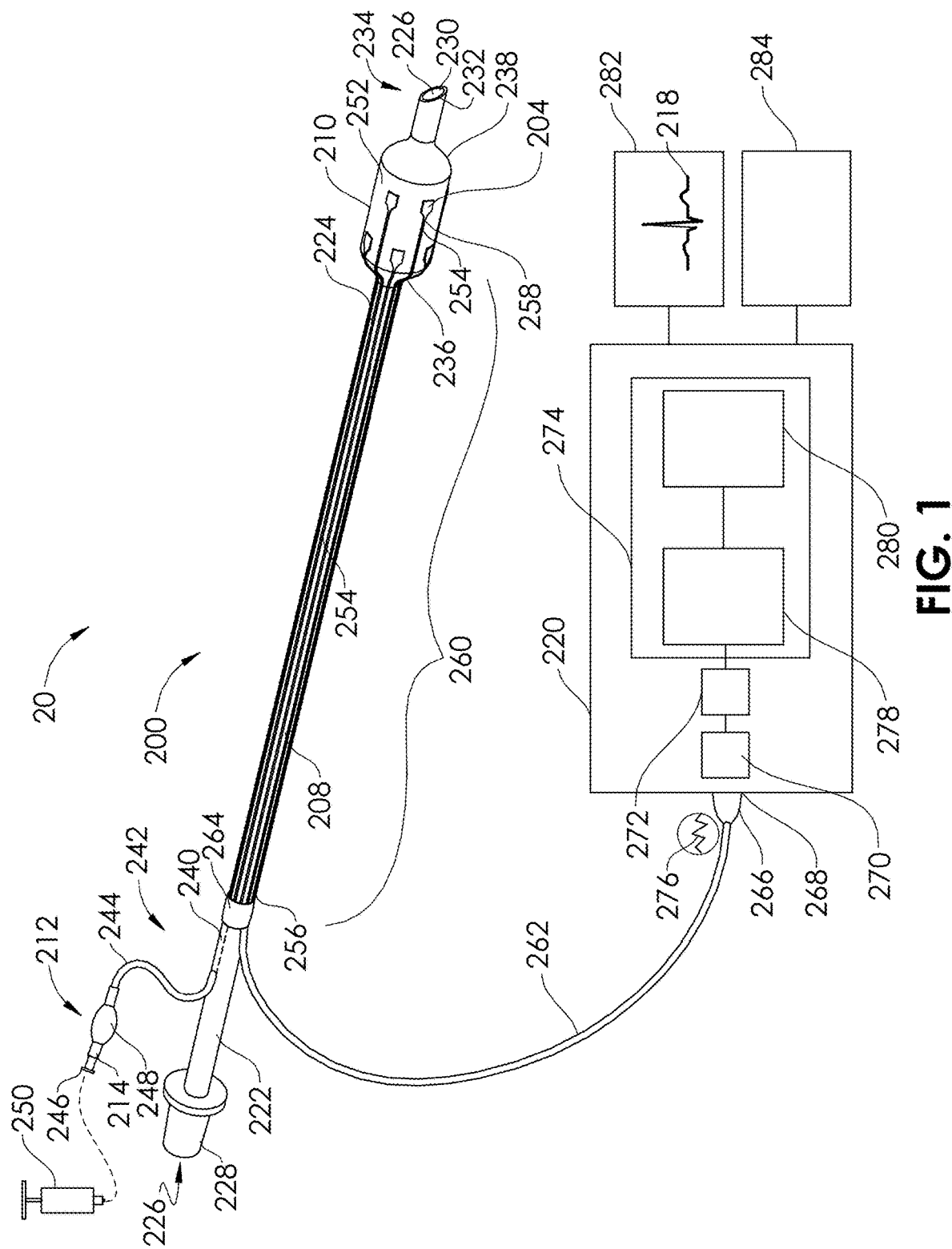
FIG. 1 is a perspective view of a system for sensing electrical activity of the heart according to an embodiment of the present disclosure.

Embodiments of the invention include an approach for acquiring signals for measuring electrical activity of the heart, such as ECG signals that includes measurement from at least one or more portions of the body of a subject that do not include the skin. The one or more portions of the body can include internal portions of the body, such as portions within naturally occurring orifices or body cavities or lumens, or even a cavity of the body caused by trauma. In certain embodiments, one or more electrically conductive "sensor" pads or electrodes are deposited/printed to/or attached to a sensing device that is configured to be inserted into a body orifice, cavity or lumen. Some examples of body lumens include, but are not limited to the trachea or esophagus of a patient. Each sensor is configured to constitute a lead that provides a component of an ECG circuit. The ECG circuit may include one of these components or more than one of these components. In some cases, the leads created from the sensors/electrodes of a sensing device may replace traditional leads, such as one or more leads of a "12 lead" ECG system. In addition to the sensors on the sensing device, one or more auxiliary sensor may also be used. The one or more auxiliary sensor may be placed in contact with the subject's tongue, soft palate, nostril/nasal passage, cheek, anus, urethra or any other location which allows contact with the subject's mucosa (i.e., mucous membrane). In some cases, the auxiliary sensor may be applied externally, for example, on the subject's shoulder. The sensors may be carried on the sensing device on a surface comprising a membrane, balloon, or cuff that can be inflated to press the sensors into contact with the mucosal lining of the trachea or esophagus. The sensors may also be carried on an elongate member of the sensing device (body, shaft), which may be configured to be changed from a linear or substantially linear low-profile state to an expanded state having a enlarged state in comparison with the elongate member of the sensing device. In some embodiments, by placing one or more sensors at points on the device and one auxiliary sensor (for example, on the tongue or externally on the shoulder), an ECG signal can be acquired. In some embodiments the sensing device may include two or more sensors, and may be used with a single auxiliary sensor. In some embodiments, the sensing device may include a single sensor and may be used with two or more auxiliary sensors. The use of a sensing device which comprises sensors for placement on internal structures has the benefit of placing the sensors in contact with electrically conductive moist tissue, thus allowing immediate, reliable electrical coupling. This precludes the need for specially conductive gel placement and may also remove the need to apply the separate ECG pads as currently used or having to individually connect each sensor to a cable. Such a device can be quickly placed into a body lumen, cavity or orifice, and expanded (e.g., inflated) thereby immediately acquiring the ECG signal.

This approach allows one to acquire a multi-lead ECG signal from a patient without the need for attachment site preparation and individual cable connections. It also improves the electrical contact by making contact with moist mucosal membranes instead of relying exclusively on external (resistive) skin surfaces. As many patients needing ECG measurement typically receive either a tracheal tube (endotracheal tube) or a nasogastric tube (NG tube), there is no increased invasiveness of this procedure. Besides the endotracheal tube or NG tube, other types of devices may be incorporated into the sensing devices taught herein, such as a laryngeal mask, a gastric lavage tube, a gastric aspiration tube, or a gastric decompression tube, including, but not limited to an Ewald orogastric tube, a Lavacutor® orogastric tube, an Edlich orogastric tube, a sump tube, such as a Salem tube, a Levin tube, gastric suction/feeding tubes, such as a Moss Mark IV nasal tube, a Dobbhoff nasojejunal feeding and gastric decompression tube, a nasointestinal tube such as a Miller-Abbott tube, and a treatment tube such as a Sengstaken-Blakemore tube.

FIG. 1 illustrates a sensing system 20 comprising a sensing device 200 which is configured to be coupled to a console 220. The sensing system 20 is configured to sense signals from the interior of a subject. Such signals may include signals related to electrical activity of the heart, such as can be acquired to provide an electrocardiogram. The sensing device 200 comprises an elongate member 208, which may comprise a shaft or catheter tubing. The elongate member 208 has a proximal end 222 and a distal end 224. The sensing device 200 as depicted in FIG. 1 is configured to serve as an endo-tracheal tube, and thus the sensing device 200 comprises a respiratory lumen 226 extending between a fitting 228, coupled to the proximal end 222 of the elongate member 208 and a port 230 adjacent the distal end 224 of the elongate member 208. The respiratory lumen 226 may be configured to allow the passage of a guidewire (not shown), which may be placed through the respiratory lumen 226 to aid in the delivery of the sensing device 200 within the body cavities of the subject, and which may be subsequently removed. At the port 230, the elongate member 208 may include a skive 232, or angled cut or form, to aid in the tracking of the distal end 234 of the sensing device 200. The fitting 228 is configured to couple to a respiratory or other oxygen or air delivery apparatus, for delivering oxygen and other gases, which may in some cases include an anesthetic, through the respiratory lumen 226 and out the port 230 in into the patient's lungs, for example via the trachea and/or bronchi.

An actuation portion 210 having a proximal end 236 and a distal end 238 is carried by the distal end 224 of the elongate member 208, or may be actually formed from the distal end 224 of the elongate member 208. The actuation portion 210 may comprise an inflatable member, such as a balloon or cuff, or an otherwise expandable structure, and can be configured to have a low-profile state for placement into a body lumen or cavity and delivery within the body lumen or cavity (or within the lumen of a sheath or tube, including a catheter tube). The inflatable member and the elongate member 208 may comprise a polymer such as polyvinyl chloride (PVC) or polyethylene. The actuation portion 210 can also have an expanded state. If the actuation portion 210 is an inflatable member, then the expanded state may be achieved by inflating the actuation portion 210 (inflatable member) with a fluid, such as a gas or liquid. The fluid may include, for example, water, normal saline, air, nitrogen, or other inflation media. An inflation lumen 240 extends from a proximal location 242 to the actuation portion 210 (inflatable member) and is accessed at an interface 212, which may be coupled to the inflation lumen 240 via extension tubing 244. The interface 212 may comprises a luer fitting 246 configured to attach to a syringe or other type of inflation device 250. The interface 212 may include a valve 214, such as a luer-activated valve. The luer-activated valve may be configured to be in a closed (sealed) state when no inflation device is attached to the luer fitting 246, and may be configured to be in an open (unsealed) state when an inflation device is attached to the luer fitting 246. A pilot balloon 248 may be carried on the interface 212 to give tactile or visual feedback for a user to determine the extent of inflation of the inflatable member.

In FIG. 1, the actuation portion 210 is an inflatable member which carries one of more sensors 204 on its surface 252. The one or more sensors 204 are secured to the surface 252 of the actuation portion 210 by adhesive or epoxy, or the one of more sensors 204 may be deposited, painted, coated, sprayed, sputtered, or otherwise attached or adhered to the surface 252. In some embodiments, the one or more sensors 204 may be applied to the surface 252 of the actuation portion 210 by use of a masking process described herein. In other embodiments, the one or more sensors 204 may be applied by a computer-controlled or robotic applicator which applies the sensor 204 in a computer-controlled pattern to the surface 252. In some embodiments, the one or more sensors 204 are electrodes comprising an electrically conductive material, which may comprises silver, such as a conductive silver ink, carbon ink, a silver-silver chloride ink, or a silver-carbon-silver chloride ink. In some embodiments, a radiopaque ink may be applied along with or adjacent the electrically conductive inks, or may even be the electrically conductive ink. The radiopaque ink increases the ability, for example, to visualize the one or more sensors 204 under radiography or fluoroscopy.

Each of the one or more sensors 204 may be coupled to a conductor 254 having a proximal end 256 and a distal end 258. The one or more conductors 254 may be applied to the actuation portion 210 and the elongate member 208 by the same process with which the one or more sensors 204 are applied to the actuation portion 210. The one or more conductors 254 may be applied at the same time as the one or more sensors 204 or may be applied before or after the application of the one or more sensors 204. In some embodiments, the one or more sensors 204 are partially applied (e.g., a single layer or a first number of layers), the one or more conductors 254 are then applied, and then a final one or more layers are applied to complete the on ore more sensors 204. In some embodiments, a dielectric layer 260 is subsequently applied over the one or more conductors 254 after the application of the one or more conductors 254. A cable 262 is electrically coupled to the proximal ends 256 of the one or more conductors 254 (for example, with solder), and a covering or strain relief 264 may be secured over the area of connection. The covering or strain relief 264 may be a dielectric material, including polyimide, adhesive or epoxy, polyethylene or polyester shrink tubing or other similar materials or combinations thereof.

The cable 262 includes a connector 266 which is configured to be coupled to an input 268 of the console 220 and is configured to carry signals 276 from the one or more sensors 204 to the console 220. Signals 276 entering the console 220 may in some embodiments represent several different sensors 204 (having been carried by several corresponding conductors 254). In some embodiments, the console 220 may include a lead selector 270 to allow selection of a signal 276 from a particular one of the one or more sensors 204. In some embodiments, one or more signals 276 from one or more sensors 204 may be processed in parallel. The console 220 may include a protection circuit 272, which may include a circuit breaker or other circuit protection device. The one or more signals 276 may enter a processor 274 provided by the console 220. The processor 274 may include one or more amplifiers 278 for amplifying the signal 276 and one or more filters 280 for filtering the signal 276. A display 282 is configured to display a resulting electrocardiogram signal 218 or trace (e.g., PQRST waveform) from the console 220. The display 282 may be built in to the console 220 or may be separate. The display 282 may be directly connect to the console 220 or may be remote and communicate wirelessly. The console 220 may include an interface 284 which allows a user to control and/or communicate with the console 220 or the sensing system 20 in general. The interface may even allow a user to control or communicate with the sensing device 200, for example, if the sensing device 200 incorporates an internal microprocessor, which may be carried on a flex circuit. The interface 284 may be a touch screen, a keyboard, an audio communication system (e.g., voice-activated), and may incorporate a graphic user interface (GUI).

Figure 2:
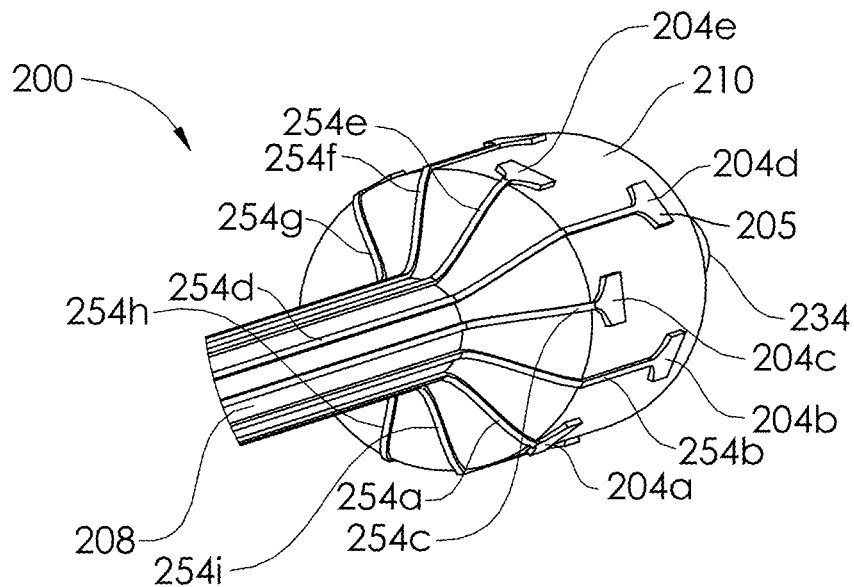
FIG. 2 is a perspective view of an actuation portion of a sensing device of the system of FIG. 1.

FIG. 2 shows the actuation portion 210 in greater detail. The actuation portion 210 includes several of the one or more sensors 204*a*, 204*b*, 204*c*, 204*d*, 204*e* with the corresponding conductors 254*a*, 254*b*, 254*c*, 254*d*, 254*e* extending from the sensors 204*a-e* and proximally along the actuation portion 210 and the elongate member 208. Each of the sensors 204*a-e* may be located at different positions along the actuation portion 210 that are more distal or more proximal in relation to others of the sensors 204*a-e*. In addition, each of the sensors 204*a-e* may be located at different rotational orientations (e.g., 0° to 360°) in relation to others of the sensors 204*a-e*. In FIG. 2, although five sensors 204*a-e* are labeled, the embodiment is intended to have nine separate sensors 204 connected to nine conductors 254*a-i*. Each of the one or more sensors 204*a-e* has a contact surface 205 which is configured to contact an interior wall of a body lumen, duct, or cavity. The orientation (of the sensors 204) may be varied in different embodiments, in order to obtain signals that have relation to different portions of a patient's heart muscle and conduction system, thus allowing the diagnosis of disorders affecting various portions of the heart. For example, infarct may be identified to be located in one or more of the coronary arteries or side branches, such as the Left Anterior Descending coronary artery (LAD), Right coronary artery (RCA), Circumflex coronary artery (Cx) or even particular marginal or diagonal branches.

Figure 3:
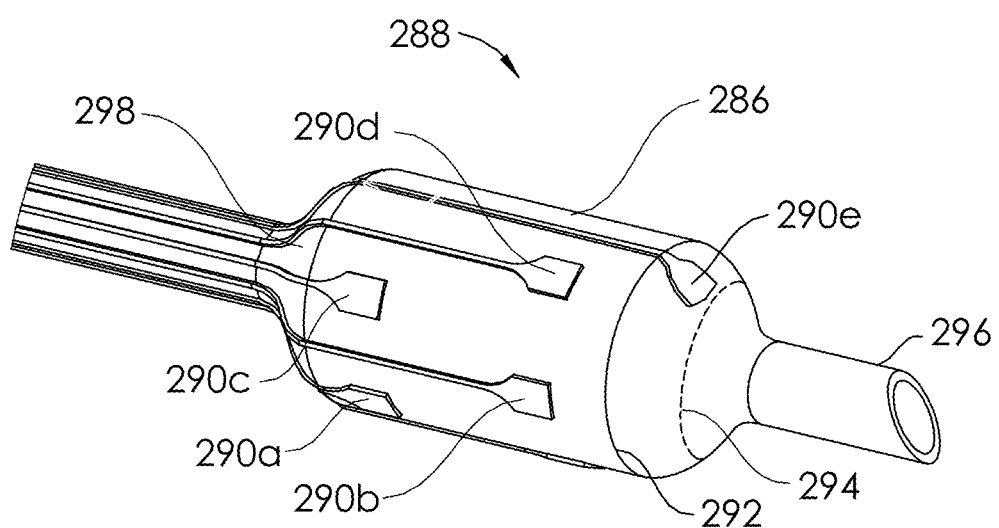
FIG. 3 is a perspective view of an alternative embodiment of an actuation portion of a sensing device.

FIG. 3 illustrates an alternative embodiment of the actuation portion 286 of a sensing device 288 having a series of sensors 290*a-e*. Though sensors 290*a-d* are carried on a maximal diameter portion 292 of the actuation portion 286, sensor 290*e* extends to a smaller diameter 294, when the actuation portion 286 is in its expanded state (as shown). This particular embodiment may be configured for use in a body lumen or vessel whose inner diameter tapers to a smaller diameter distally, so that the sensor 290*e* is carried by the actuation portion 286 at the appropriate smaller diameter of the distal lumen or vessel. Alternatively, the actuation portion 286 may be purposely oversized in relation to the target body lumen or vessel, and thus configured to be overinflated or overexpanded. This may be appropriate with body vessels with walls that are compliant, such that, when the actuation portion 286 is in its expanded state, the sensor 290*e* is still capable of creating a contact with the interior wall of the body lumen or vessel. The sensor 290*e* is located near the smaller diameter 294 which is oriented towards the distal end 296 of the sensing device 288, but in alternative embodiments, the sensor 290*e* may be located at a smaller diameter portion that is towards the proximal end 298 of the actuation portion 286. In some embodiments, the sensing device 288 may be configured such that a first pressure causes sensors 290a, 290b, 290c, 290d to contact an interior wall of the body lumen or cavity, but not the sensor 290e, and such that a second, higher pressure causes sensor 290e to also contact the interior wall of the body lumen or cavity.

Figure 4:
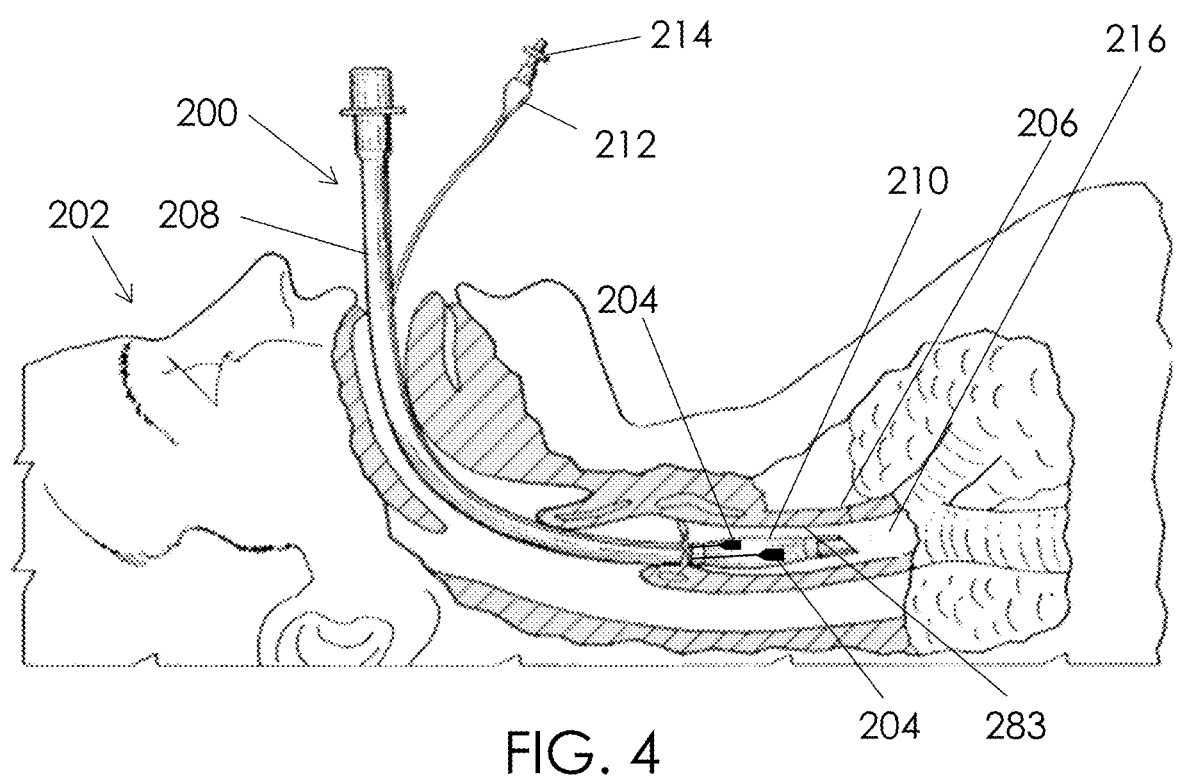
FIG. 4 is a partial sectional view of a sensing device placed within a trachea of a subject according to an embodiment of the present disclosure.
Figure 5:
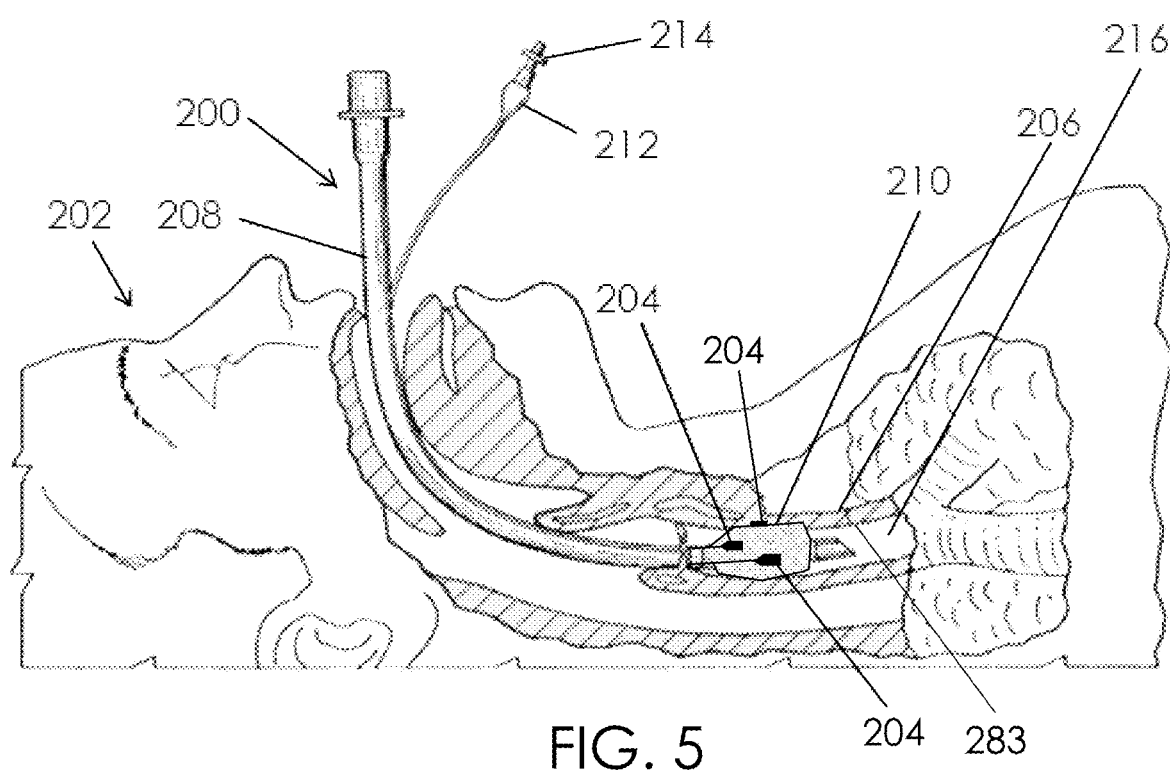
FIG. 5 is a partial sectional view of the sensing device of FIG. 4 having an actuation portion in an expanded state.

FIG. 4. Illustrates the sensing device 200 in place within a patient 202, such that the actuation portion 210 is within a lumen 216 of the trachea 206 while it its low-profile or deflated state. In use, a user inserts the sensing device into the patient's mouth and advances the actuation portion 210 into the trachea 206. By attaching an inflation device (e.g., syringe) to the interface 212, the user may inflate the actuation portion 210 (e.g., balloon, cuff) (FIG. 5) such that the sensors 204 (e.g., electrodes) contact in interior wall 283 of the trachea 206. The valve 214 maintains the desired inflated pressure, and thus maintains the contact of the sensors 204 with the interior wall 283 of the trachea 206. Because the sensors 204 are contacting the soft tissue of the interior wall 283, an acceptable electrical contact is made without the need for coupling gel or liquid. The maintenance of pressure inside the actuation portion 210 assures that the electrical contact between the sensors 204 and the interior wall 283 is not interrupted. This is in contrast to traditional electrode pads that are carried by the skin which typically incorporate a coupling gel, and which nevertheless can be accidentally pulled off, scraped off or can fall off because of sweating or contamination (spilling, etc.) in the application area.

Figure 6:
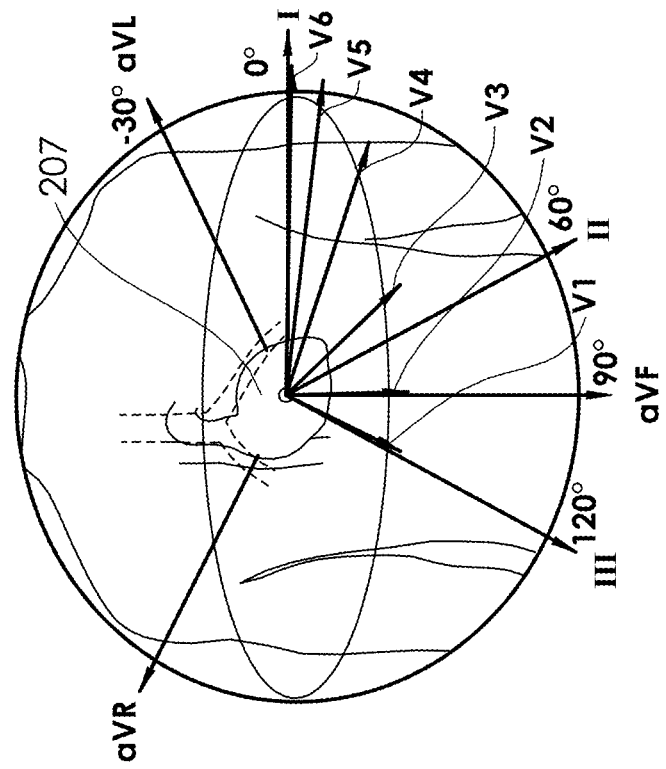
FIG. 6 is a perspective view of approximated ECG vectors for a "12 lead" electrocardiographic system.

FIG. 6 illustrates a three-dimensional array of vectors of a traditional "12 lead" ECG. This is a simplified depiction, and the heart 207 is not necessarily to scale or in its actual location in the torso. Ten external skin electrodes (sensors) are typically placed, four on the limbs (left arm, right arm, left leg right leg) and six on the chest area (1-6). The resulting twelve leads include dipolar leads I, II, III (which can be pictorially superpositioned to represent what is known as the Einthoven Triangle) and unipolar leads aVR (augmented voltage right), aVL (augmented voltage left), aVF (augmented voltage foot), V1, V2, V3, V4, V5, V6 (from the six chest area electrodes).

Figure 7:
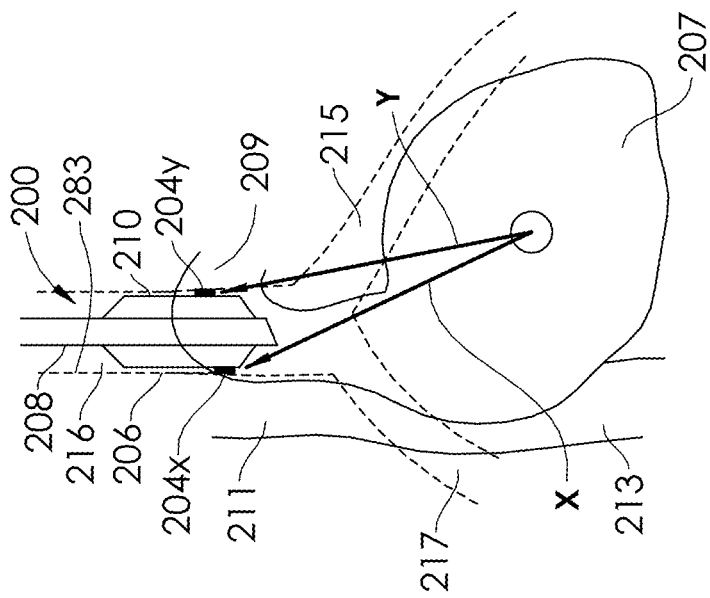
FIG. 7 is a view of a sensing device placed within the trachea of a subject according to an embodiment of the present disclosure.

A sensing device 200 is shown in FIG. 7 having sensors 204x, 204y disposed on its actuation portion 210 and located and expanded within the lumen 216 of the trachea 206. Each of the sensors 204x, 204y are contacting the interior wall 283 of the trachea 206, thus being electrodes for lead X and lead Y, respectively. A first vector X indicates lead X and vector Y indicates lead Y. For reference purposes the aorta 209, superior vena cava 211, inferior vena cava 213 and two bronchi 215, 217 are illustrated.

Figure 8:
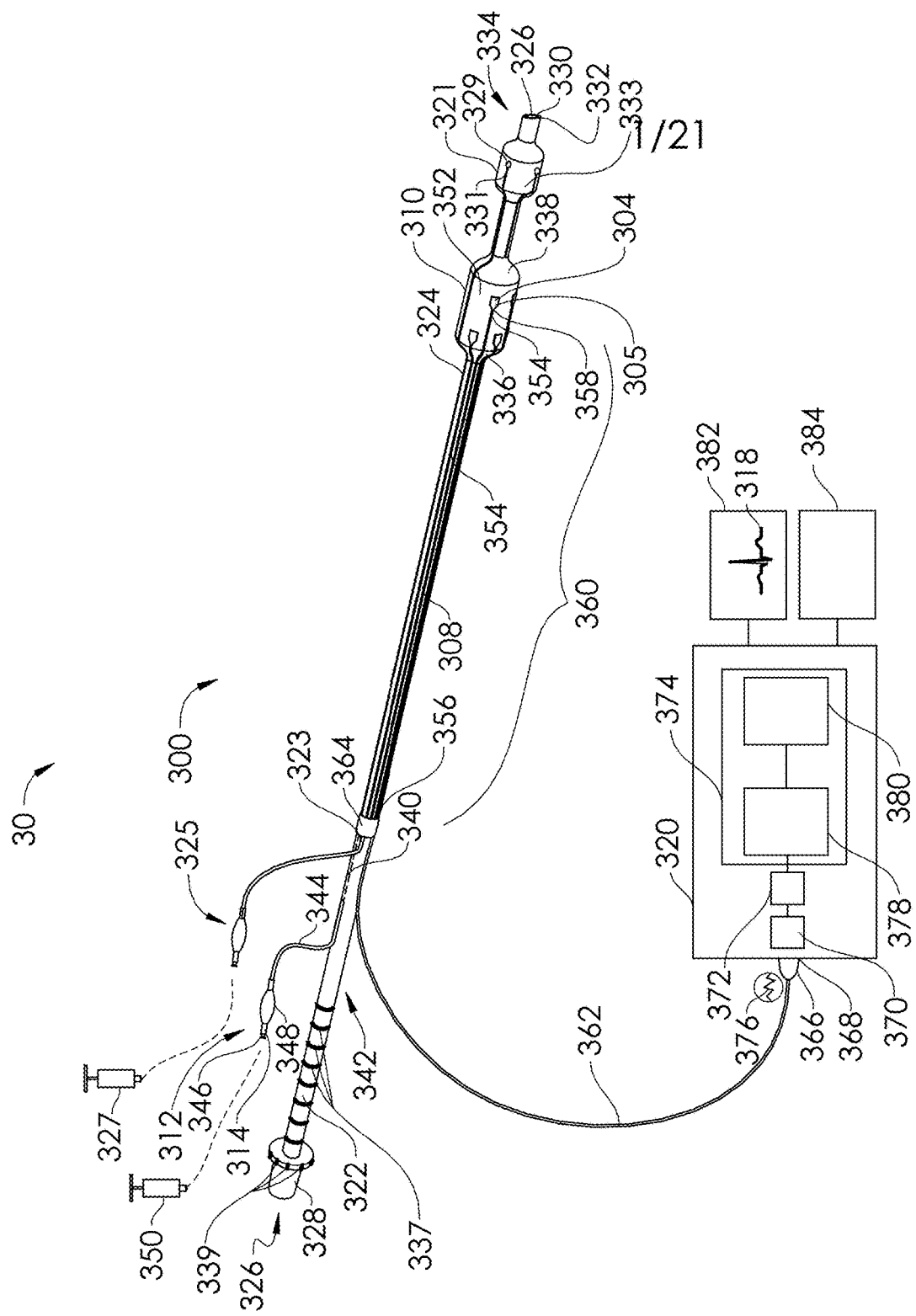
FIG. 8 is a perspective view of a system for sensing electrical activity of the heart according to an embodiment of the present disclosure.

FIG. 8 illustrates a sensing system 30 comprising a sensing device 300 which is configured to be coupled to a console 320. The sensing system 30 is configured to sense signals from the interior of a subject. Such signals may include signals related to electrical activity of the heart, such as can be acquired to provide an electrocardiogram. The sensing device 300 comprises an elongate member 308, which may comprise a shaft or catheter tubing. The elongate member 308 has a proximal end 322 and a distal end 324. The sensing device 300 as depicted in FIG. 8 is configured to serve as an endo-tracheal tube having sub-selective capability, and thus the sensing device 300 comprises a respiratory lumen 326 extending between a fitting 328, coupled to the proximal end 322 of the elongate member 308 and a port 330 adjacent the distal end 324 of the elongate member 308. The respiratory lumen 326 may be configured to allow the passage of a guidewire (not shown), which may be placed through the respiratory lumen 326 to aid in the delivery of the sensing device 300 within the body cavities of the subject, and which may be subsequently removed. At the port 330, the elongate member 308 may include a skive 332, or angled cut or form, to aid in the tracking of the distal end 334 of the sensing device 300. The fitting 328 is configured to couple to a respiratory or other oxygen or air delivery apparatus, for delivering oxygen and other gases, which may in some cases include an anesthetic, through the respiratory lumen 326 and out the port 330 in into the patient's lungs, for example via one or more bronchi.

A first actuation portion 310 having a proximal end 336 and a distal end 338 is carried by the distal end 324 of the elongate member 308, or may be actually formed from the distal end 324 of the elongate member 308. The first actuation portion 310 may comprise an inflatable member, such as a balloon or cuff, or an otherwise expandable structure, and can be configured to have a low-profile state for placement into a body lumen or cavity and delivery within the body lumen or cavity (or within the lumen of a sheath or tube, including a catheter tube). The first actuation portion 310 can also have an expanded state. If the first actuation portion 310 is an inflatable member, then the expanded state may be achieved by inflating the first actuation portion 310 (inflatable member) with a fluid, such as a gas or liquid. The fluid may include, for example, water, normal saline, air, nitrogen, or other inflation media. An inflation lumen 340 extends from a proximal location 342 to the first actuation portion 310 (inflatable member) and is accessed at an interface 312, which may be coupled to the inflation lumen 340 via extension tubing 344. The interface 312 may comprises a luer fitting 346 configured to attach to a syringe or other type of inflation device 350. The interface 312 may include a valve 314, such as a luer-activated valve. The luer-activated valve may be configured to be in a closed (sealed) state when no inflation device is attached to the luer fitting 346, and may be configured to be in an open (unsealed) state when an inflation device is attached to the luer fitting 346. A pilot balloon 348 may be carried on the interface 312 to give tactile or visual feedback for a user to determine the extent of inflation of the inflatable member. Distal to the first actuation portion 310 is a second actuation portion 321 which is expandable. The second actuation portion 321 may be an inflatable member, such as a balloon or cuff, and may be expandable through the same inflation lumen 340 as the first actuation member 310, or, as illustrated, may be independently expandable through a second inflation lumen 323 via a second interface 325, which may have similar features to the interface 312. For example, the second interface 325 may be inflated by an inflation device 327. In some embodiments, the first actuation member 310 may be configured to be inflated within a trachea 206 while the second actuation portion 321 may be configured to be inflated within a bronchi 215, 217. In some embodiments, the first actuation portion 310 has a larger profile or diameter than the second actuation portion 321. For example, the diameter of the first actuation portion 310 may be between about 5 mm and about 30 mm, or between about 13 mm and about 27 mm, while the diameter of the second actuation portion 321 may be between about 4 mm and 20 mm, or between about 9 mm and about 18 mm.

In FIG. 8, the first actuation portion 310 is an inflatable member which carries one of more sensors 304 on its surface 352. The one or more sensors 304 may be secured to the surface 352 of the first actuation portion 310 by adhesive or epoxy, or the one or more sensors 304 may be deposited, painted, coated, sprayed, sputtered, or otherwise attached or adhered to the surface 352. In some embodiments, the one or more sensors 304 may be applied to the surface 352 of the first actuation portion 310 by use of a masking process described herein. In other embodiments, the one or more sensors 304 may be applied by a computer-controlled or robotic applicator which applies the sensor 304 in a computer-controlled pattern to the surface 352. In some embodiments, the one or more sensors 304 are electrodes comprising an electrically conductive material, which may comprises silver, such as a conductive silver ink, carbon ink, a silver-silver chloride ink, or a silver-carbon-silver chloride ink. In some embodiments, a radiopaque ink may be applied along with or adjacent the electrically conductive inks, or may even be the electrically conductive ink. The radiopaque ink increases the ability, for example, to visualize the one or more sensors 304 under radiography or fluoroscopy.

The one or more sensors each have a contact surface 305. Each of the one or more sensors 304 may be coupled to a conductor 354 having a proximal end 356 and a distal end 358. The one or more conductors 354 may be applied to the first actuation portion 310 and/or the elongate member 308 by the same process with which the one or more sensors 304 are applied to the first actuation portion 310. In some embodiments, the one or more sensors 304 and/or the one or more conductors 354 may be applied using methods described in U.S. Pat. No. 9,289,141 entitled "Apparatus and Methods for the Measurement of Cardiac Output," issued Mar. 22, 2016, which is hereby incorporated by reference in its entirety for all purposes. The one or more conductors 354 may be applied at the same time as the one or more sensors 304 or may be applied before or after the application of the one or more sensors 304. In some embodiments, the one or more sensors 304 are partially applied (e.g., a single layer or a first number of layers), the one or more conductors 354 are then applied, and then a final one or more layers are applied to complete the on ore more sensors 304. In some embodiments, a dielectric layer 360 is subsequently applied over the one or more conductors 354 after the application of the one or more conductors 354. One or more sensors 329 and one or more conductors 331 are applied to a surface 333 of the second actuation portion 321 by any of the methods described. The one or more conductors 331 may also be coated or otherwise covered by a dielectric material. The one or more conductors 331 may extend proximally within the interior of the elongate member 308, or may extend along with the one or more conductors 354 along an outer surface of the elongate member 308. A cable 362 is electrically coupled to the proximal ends 356 of the one or more conductors 354 and to proximal ends 335 of the one or more conductors 331 (for example, with solder), and a covering or strain relief 364 may be secured over the area of connection. The covering or strain relief 364 may be a dielectric material, including polyimide, adhesive or epoxy, polyethylene or polyester shrink tubing or other similar materials or combinations thereof.

The cable 362 includes a connector 366 which is configured to be coupled to an input 368 of the console 320 and is configured to carry signals 376 from the one or more sensors 304 and/or one or more sensors 329 to the console 320. Signals 376 entering the console 320 may in some embodiments represent several different sensors 304, 329 (having been carried by several corresponding conductors 354, 331). In some embodiments, the console 320 may include a lead selector 370 to allow selection of a signal 376 from a particular one of the one or more sensors 304, 329. In some embodiments, one or more signals 376 from one or more sensors 304, 329 may be processed in parallel. The console 320 may include a protection circuit 372, which may include a circuit breaker or other circuit protection device. The one or more signals 376 may enter a processor 374 provided by the console 320. The processor 374 in some embodiments includes one or more amplifiers 378 for amplifying the signal 376 and one or more filters 380 for filtering the signal 376. A display 382 is configured to display a resulting electrocardiogram signal 318 or trace (e.g., PQRST waveform) from the console 320. The display 382 may be built in to the console 320 or may be separate. The display 382 may be directly connect to the console 320 or may be remote and communicate wirelessly. The console 320 may include an interface 384 which allows a user to control and/or communicate with the console 320 or the sensing system 30 in general. The interface may even allow a user to control or communicate with the sensing device 300, for example, if the sensing device 300 incorporates an internal microprocessor, which may be carried on a flex circuit. The interface 384 may be a touch screen, a keyboard, an audio communication system (e.g., voice-activated), and may incorporate a graphic user interface (GUI).

In some embodiments, an additional sensor may be carried on the second actuation portion 321 which is configured to measure venous oxygenation. The additional sensor may comprise an optical oxygen saturation sensor.

Figure 9:
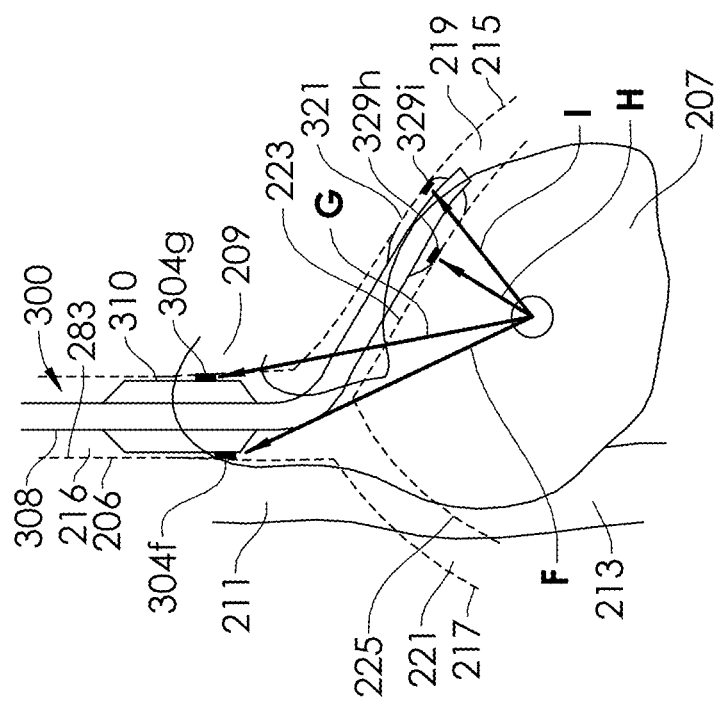
FIG. 9 is a view of a sensing device placed within the trachea and a bronchus of a subject according to an embodiment of the present disclosure.

A sensing device 300 is shown in FIG. 9 having sensors 304*f*, 304*g* disposed on its first actuation portion 310 which has been located and expanded within the lumen 216 of the trachea 206. In addition, sensors 329*h*, 329*i* are disposed on the second actuation portion 321 of the sensing device 300, and the second actuation portion 321 has been located and expanded within a lumen 219 of left bronchus 215. Each of the sensors 304*f*, 304*g* are contacting the interior wall 283 of the trachea 206, thus being electrodes for lead F and lead G, respectively. A first vector F indicates lead F and vector G indicates lead G. Each of the sensors 329*h*, 329*i* are contacting an interior wall 223 of the left bronchus 215, thus being electrodes for lead H and lead I, respectively. Vector H indicates lead H and vector I indicates lead I.

Figure 10:
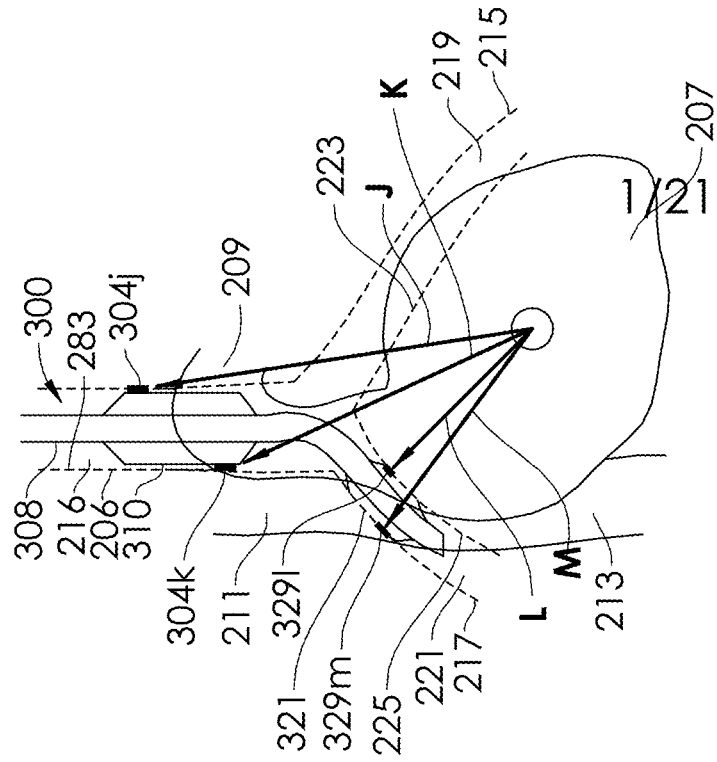
FIG. 10 is a view of a sensing device placed within the trachea and a bronchus of a subject according to an embodiment of the disclosure.

A sensing device 300 is shown in FIG. 10 having sensors 304*j*, 304*k* disposed on its first actuation portion 310 which has been located and expanded within the lumen 216 of the trachea 206. In addition, sensors 329*l*, 329*m* are disposed on the second actuation portion 321 of the sensing device 300, and the second actuation portion 321 has been located and expanded within a lumen 221 of right bronchus 217. Each of the sensors 304*j*, 304*k* are contacting the interior wall 283 of the trachea 206, thus being electrodes for lead J and lead K, respectively. Vector J indicates lead J and vector K indicates lead K. Each of the sensors 329*l*, 329*m* are contacting an interior wall 225 of the right bronchus 217, thus being electrodes for lead L and lead M, respectively. Vector L indicates lead L and vector M indicates lead M. As can be seen with either in either of the positions of the sensing device 300 illustrated in FIGS. 9 and 10, moving the second actuation portion 321 either deeper into the bronchi 215, 217 or less deep (by collapsing/deflating the second actuation portion 321, advancing or retracting the sensing device 300, and re-expanding/inflating the second actuation portion 321) will change the orientation or angle of the vectors H, I, L, M. The change in orientation or angle of the vectors H, I, L, M can be capable or varying the portion of the heart 207 being sensed by the sensors 329*h*, 329*i*, 329*l*, 329*m*. The vectors F, G, J, K may likewise be adjusted by advancing or retracting the sensing device 300 to move the first actuation portion 310 distally or proximally, thus changing the location of sensors 304*f*, 304*g*, 304*j*, 304*k*. Returning to FIG. 8, depth markings 337 carried by the elongate member 308 allow precision placement and adjustment of the longitudinal location of the sensing device 300 and the first and second actuation portions 310, 321. The depth markings 337 may each be separated by 20 mm, 10 mm, 5 mm, or even 1 mm, or any distance between. Each depth marking 337 may be made similar to the other depth markings 337, or each may differ with the others, for specific identification. The depth markings 337 may be applied by any manner known in the art, such as pad printing, marking, colored shrink tubing, scoring, or other acceptable manners.

Additionally, by rotating the sensing device 300, the rotational orientation of the sensors 329h, 329i, 329l, 329m of the second actuation portion 321 and the sensors 304f, 304g, 304j, 304k of the first actuation portion 310 may also be changed, thus changing the orientation or angle of vectors H, I, L, M, F, G, J, K, respectively. Again, the portion of the heart 207 may thusly be set or adjusted in this manner. Circumferentially-arrayed markings 339 (FIG. 8) may be carried by the elongate member 308, or as illustrated, the fitting 338. The circumferentially-arrayed markings 339 may be applied by any manner known in the art, such as pad printing, marking, colored shrink tubing, scoring, or other acceptable manners. A temporary mark may be made on the patient's mouth (lip, etc.) as a landmark for comparing the location of the circumferentially-arrayed markings 339, or another piece of medical equipment nearby or other adjacent object may be used as a landmark. The markings 337, 339 and the adjustment methods described may also be used with the sensing device 200 of FIG. 1, or any of the other embodiments described herein.

Figure 11:
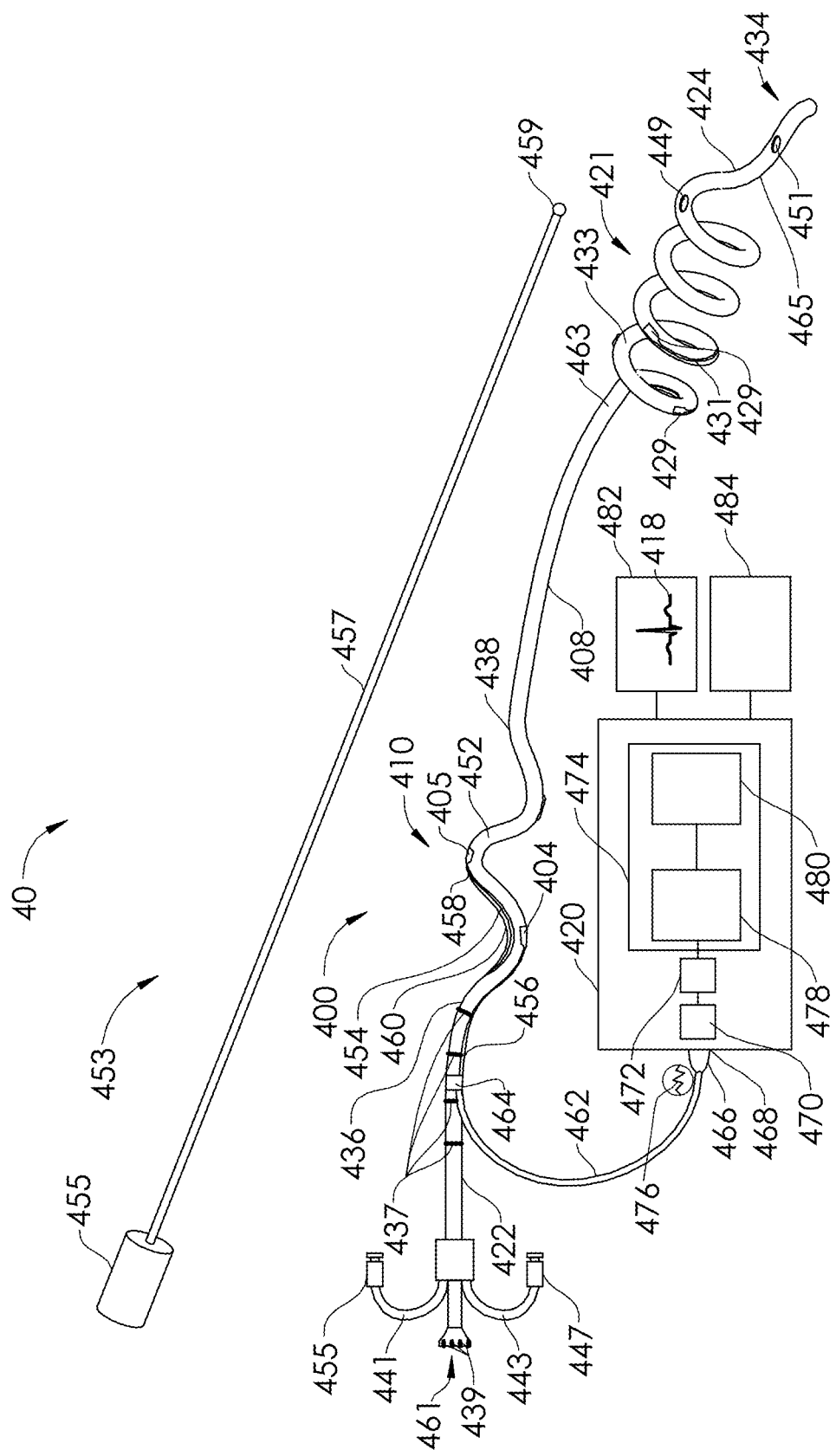
FIG. 11 is a perspective view of a system for sensing electrical activity of the heart according to an embodiment of the present disclosure.

FIG. 11 illustrates a sensing system 40 comprising a sensing device 400 which is configured to be coupled to a console 420. The sensing system 40 is configured to sense signals from the interior of a subject. Such signals may include signals related to electrical activity of the heart, such as can be acquired to provide an electrocardiogram. The sensing device 400 comprises an elongate member 408, which may comprise a shaft or catheter tubing. The elongate member 408 has a proximal end 422 and a distal end 424. The sensing device 400 as depicted in FIG. 11 is configured to serve as a nasogastric tube (NG tube), and thus the sensing device 400 comprises one or more lumens 441, 443 extending between one or more fittings 445, 447 coupled to the proximal end 422 of the elongate member 408 and extending through the elongate member until terminating at one or more ports 449, 451 adjacent the distal end 424 of the elongate member 408. One of the ports 449, 451 may be configured for delivery of one or more medicants or for delivery of other fluids (e.g., normal saline) or for delivery of enteral feeding solutions. The port 449, 451 may be located for direct delivery of the fluids into the stomach, but in alternative embodiments, the sensing device may be configured to allow at least one of the ports 449, 451 to be located in the duodenum or jejunum for direct delivery. In some cases, the port 449, 451 may be located in the distal esophagus. In some embodiments, one of the lumens 441, 443 may be dedicated to fluid delivery while the other lumen 441, 443 is dedicated to suction or lavage of internal contents, for example, stomach contents. In some embodiment, both of the lumens 441, 443 are capable of both delivery and suction or lavage. In some embodiments, the fittings 445, 447 comprises luer fittings, configured to couple to luer fittings of various delivery or suction devices.

Figure 12:
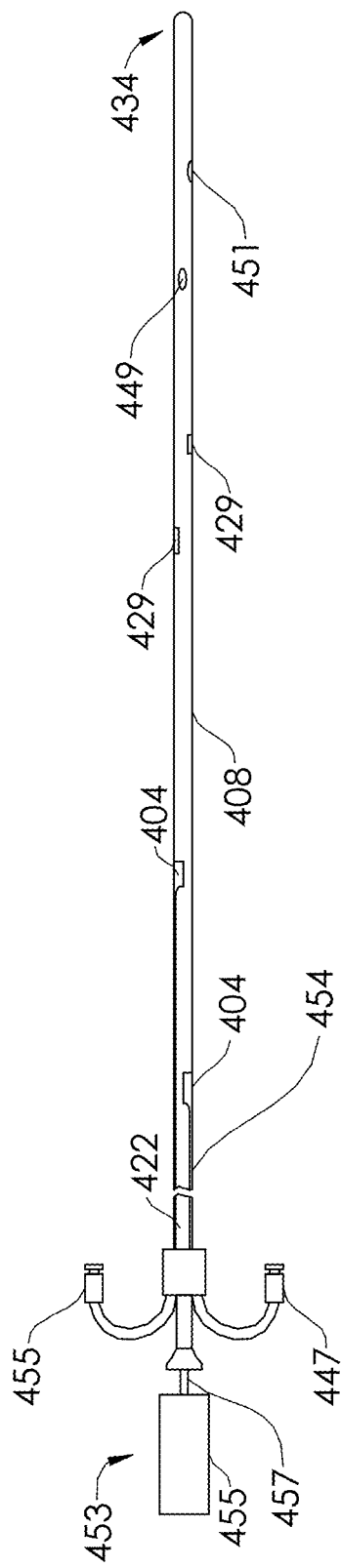
FIG. 12 is an elevation view of a sensing device of the system of FIG. 11 in a low-profile state.

A first actuation portion 410 having a proximal end 436 and a distal end 438 is carried by the elongate member 408. As illustrated in FIG. 11, the first actuation portion 410 in this particular embodiment comprises a secondary shape having an enlarged profile (in comparison to the diameter of the elongate member 408 shaft). The secondary shape is illustrated in FIG. 11 as a serpentine shape or S-shape formed directly in the elongate member 408. The shape may be formed by heat forming of a thermoplastic tubing. A stylet 453 having a proximal hub 455 and an elongate body 457 having a rounded or otherwise blunt tip 459 is configured to be placed down a central lumen 461 of the elongate member 408 of the sensing device 400. FIG. 12 illustrates the sensing device 400 with the elongate body 457 of the stylet 453 inserted within the central lumen 461, causing the first actuation portion 410 to assume a linear or substantially linear orientation, to aid in delivery or movement within a body cavity or lumen. When the sensing device 400 has been delivered to a desired location in the body lumen, for example, the esophagus and stomach, the elongate body 457 of the stylet 453 may be retracted or completely removed from the central lumen 461 of the sensing device 400, to allow the first actuation portion 410 to assume its secondary shape having an enlarged profile. In other embodiments, the elongate member 408 may comprise a shape memory polymer having shape memory which allows the first actuation portion 410 to achieve its desired secondary shape by contact with a patient's body temperature, or by introduction of a fluid having an increased temperature (e.g., 42° C.) around the elongate member 408. In another alternative embodiment, a shaped shape-memory alloy (e.g., Nitinol) resides within the elongate member 408 and causes the elongate member 408 to change shape at the first actuation portion 410 and/or the second actuation portion 421 when exposed to an elevated temperature (e.g., body temperature or an increased temperature, such as a temperature up to 42° C.). Alternatively, the first actuation portion 410 may be replaced by an inflatable member, such as a balloon or cuff such as those described in the embodiments of FIGS. 1 and 8. In general, the first actuation portion 410 comprises an expandable structure, and can be configured to have a low-profile state for placement into a body lumen or cavity and delivery within the body lumen or cavity (or within the lumen of a sheath or tube, including a catheter tube). As described, the first actuation portion 410 can also have an expanded state.

Distal to the first actuation portion 410 is a second actuation portion 421 having a proximal end 463 and a distal end 465. The second actuation portion 421 is expandable and comprises a low-profile state (FIG. 12) which may be achieved by placement of the elongate body 457 of the stylet 453 through the central lumen 461 and an expanded state (FIG. 11) which may be achieved by removal or retraction of the elongate body 457 of the stylet 453 from the central lumen 461. The secondary shape is illustrated in FIG. 11 as a spiral or helical shape formed directly in the elongate member 408. Any of the forming materials or methods used in relation to the first actuation portion 410 may also be used in relation to the second actuation portion 421. In some embodiments, the first actuation member 410 may be configured to be expanded within the esophagus while the second actuation portion 421 may be configured to be expanded within the esophagus at a location distal to the first actuation member 410. In some embodiments, the first actuation portion 410 has a smaller profile or diameter than the second actuation portion 421. For example, the (expanded) diameter of the first actuation portion 410 may be between about 15 mm and about 30 mm, or between about 20 mm and about 27 mm, while the (expanded) diameter of the second actuation portion 421 may be between about 25 mm and 40 mm, or between about 30 mm and about 37 mm. In some embodiments, both of the actuation portions 410, 421 may be spiral or helical. In some embodiments, both of the actuation portions 410, 421 may be serpentine or S-shaped. In some embodiments, the first actuation portion 410 may be spiral or helical and the second actuation portion 421 may be serpentine or S-shaped. Other three-dimensional or two-dimensional shapes may be used. In some embodiments, there may only be a single actuation portion, or in other embodiments, there may be three of more actuation portions. Though the ports 449, 451 are shown adjacent a distal end 434 of the sensing device 400, one or more ports 449, 451 may be located some distance proximal to the distal end 434, and in some embodiments proximal to the second actuation portion 421, and in some embodiments, even proximal to the first actuation portion 410. Markings 437, 439 can be utilized in the sensing device 400 as described in relation to the sensing device 300 of FIG. 8.

In FIG. 11, the first actuation portion 410 carries one of more sensors 404 on its outwardly-extending surfaces 452, such that the one or more sensors 404 are directed against an interior wall of the esophagus (or other body lumen) when the first actuation portion 410 is in its expanded state. The one or more sensors 404 may be secured to the surface 452 of the first actuation portion 410 by adhesive or epoxy, or the one of more sensors 404 may be deposited, painted, coated, sprayed, sputtered, or otherwise attached or adhered to the surface 452. In some embodiments, the one or more sensors 404 may be applied to the surface 452 of the first actuation portion 410 by use of a masking process described herein. In other embodiments, the one or more sensors 404 may be applied by a computer-controlled or robotic applicator which applies the sensor 404 in a computer-controlled pattern to the surface 452. In some embodiments, the one or more sensors 404 are electrodes comprising an electrically conductive material, which may comprises silver, such as a conductive silver ink, carbon ink, a silver-silver chloride ink, or a silver-carbon-silver chloride ink. In some embodiments, a radiopaque ink may be applied along with or adjacent the electrically conductive inks, or may even be the electrically conductive ink. The radiopaque ink increases the ability, for example, to visualize the one or more sensors 404 under radiography or fluoroscopy.

The one or more sensors each have a contact surface 405. Each of the one or more sensors 404 may be coupled to a conductor 454 having a proximal end 456 and a distal end 458. The one or more conductors 454 may be applied to the first actuation portion 410 and/or the elongate member 408 by the same process with which the one or more sensors 404 are applied to the first actuation portion 410. In some embodiments, the one or more sensors 404 and/or the one or more conductors 454 may be applied using methods described in U.S. Pat. No. 9,289,141 entitled "Apparatus and Methods for the Measurement of Cardiac Output," issued Mar. 22, 2016, which is hereby incorporated by reference in its entirety for all purposes. The one or more conductors 454 may be applied at the same time as the one or more sensors 404 or may be applied before or after the application of the one or more sensors 404. In some embodiments, the one or more sensors 404 are partially applied (e.g., a single layer or a first number of layers), the one or more conductors 454 are then applied, and then a final one or more layers are applied to complete the on ore more sensors 404. In some embodiments, a dielectric layer 460 is subsequently applied over the one or more conductors 454 after the application of the one or more conductors 454. One or more sensors 429 and one or more conductors 431 are applied to outwardly-extending surfaces 433 of the second actuation portion 421 by any of the methods described. The one or more conductors 431 may also be coated or otherwise covered by a dielectric material. The one or more conductors 431 may extend proximally within the interior of the elongate member 408, or may extend along with the one or more conductors 454 along an outer surface of the elongate member 408. The one or more conductors 454 may also extend within the interior of the elongate member 408. A cable 462 is electrically coupled to the proximal ends 456 of the one or more conductors 454 and to proximal ends of the one or more conductors 431 (for example, with solder), and a covering or strain relief 464 may be secured over the area of connection. The covering or strain relief 464 may be a dielectric material, including polyimide, adhesive or epoxy, polyethylene or polyester shrink tubing or other similar materials or combinations thereof.

The cable 462 includes a connector 466 which is configured to be coupled to an input 468 of the console 420 and is configured to carry signals 476 from the one or more sensors 404 and/or one or more sensors 429 to the console 420. Signals 476 entering the console 420 may in some embodiments represent several different sensors 404, 429 (having been carried by several corresponding conductors 454, 431). In some embodiments, the console 420 may include a lead selector 470 to allow selection of a signal 476 from a particular one of the one or more sensors 404, 429. In some embodiments, one or more signals 476 from one or more sensors 404, 429 may be processed in parallel. The console 420 may include a protection circuit 472, which may include a circuit breaker or other circuit protection device. The one or more signals 476 may enter a processor 474 provided by the console 420. The processor 474 in some embodiments includes one or more amplifiers 478 for amplifying the signal 476 and one or more filters 480 for filtering the signal 476. A display 482 is configured to display a resulting electrocardiogram signal 418 or trace (e.g., PQRST waveform) from the console 420. The display 482 may be built in to the console 420 or may be separate. The display 482 may be directly connect to the console 420 or may be remote and communicate wirelessly. The console 420 may include an interface 484 which allows a user to control and/or communicate with the console 420 or the sensing system 40 in general. The interface may even allow a user to control or communicate with the sensing device 400, for example, if the sensing device 400 incorporates an internal microprocessor, which may be carried on a flex circuit. The interface 484 may be a touch screen, a keyboard, an audio communication system (e.g., voice-activated), and may incorporate a graphic user interface (GUI).

Figure 13:
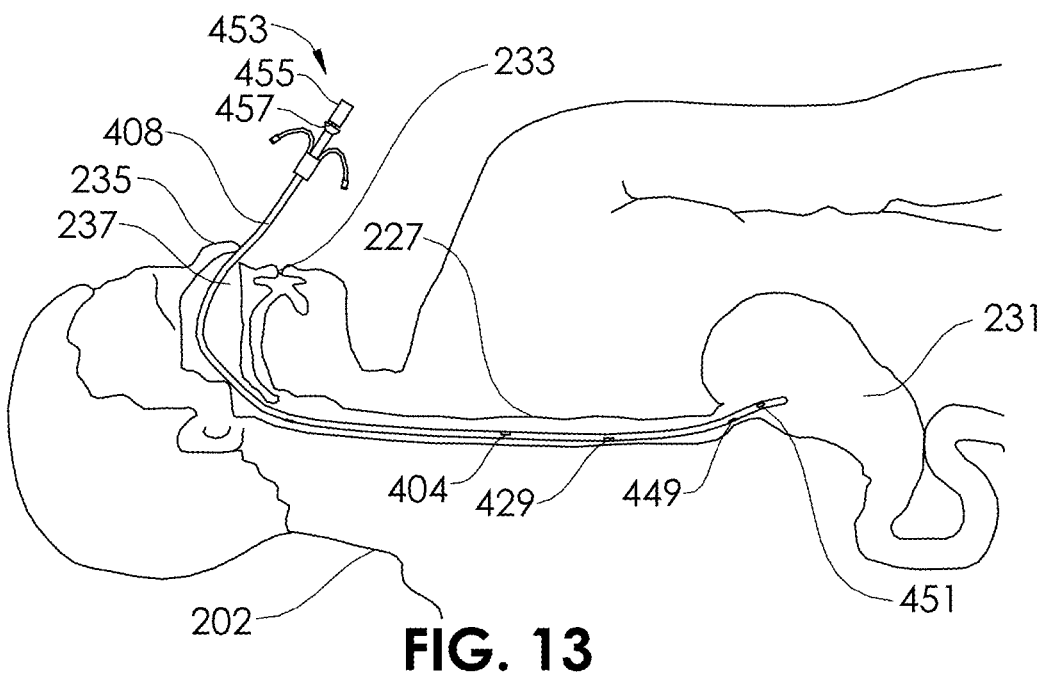
FIG. 13 is a partial sectional view of a sensing device within an esophagus of a subject in a low-profile state according to an embodiment of the present disclosure.
Figure 14:
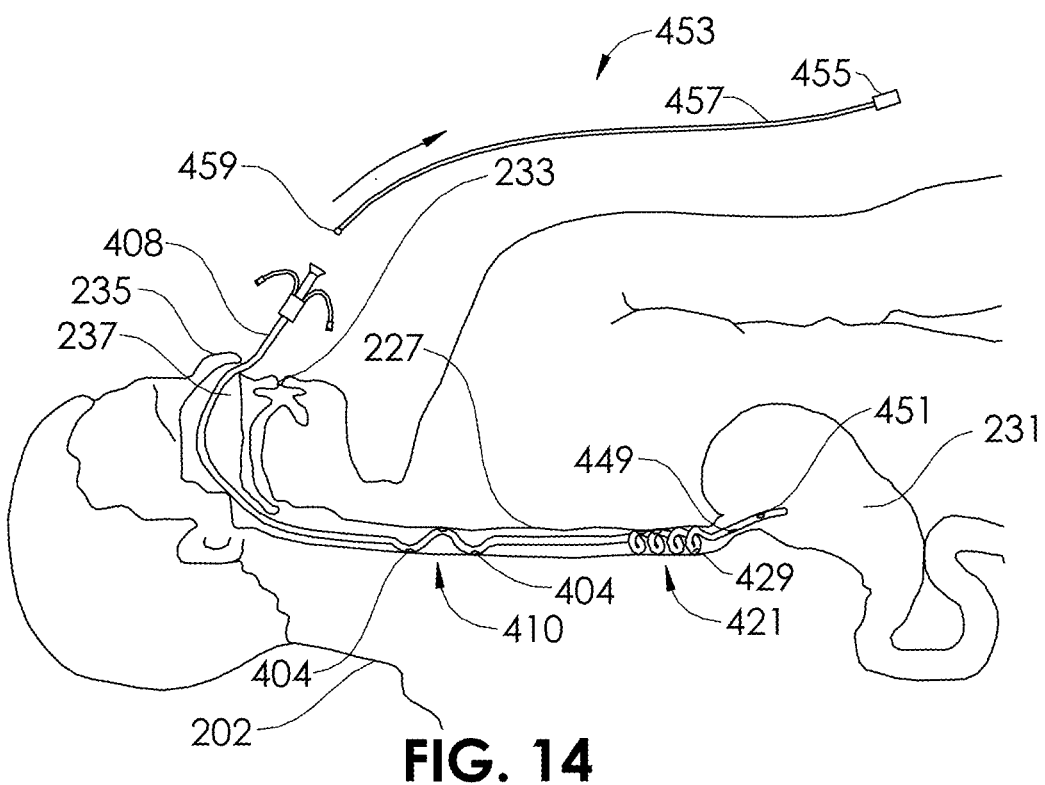
FIG. 14 is a partial sectional view of a sensing device within an esophagus of a subject in an expanded state according to an embodiment of the present disclosure.

A sensing device 400 is shown in FIG. 13 with the stylet 453 inserted inside the elongate member 408 and being delivered through the nasal cavity 237 of the nose 235 of a patient 202 and into the esophagus 227. Mouth 233 is shown as a reference point. In FIG. 14, the stylet 453 is removed from the sensing device 400 and the elongate member 408 is adjusted as necessary so that the first actuation portion 410 and second actuation portion 421 assume their secondary expanded states in their desired locations. The sensors 404, 429 are applied against interior wall portions of the esophagus 227 by the first actuation portion 410 and second actuation portion 421. Port 451 has been placed into the interior of the stomach 231 for fluid delivery, suction, lavage, or other procedural purposes.

Figure 15:
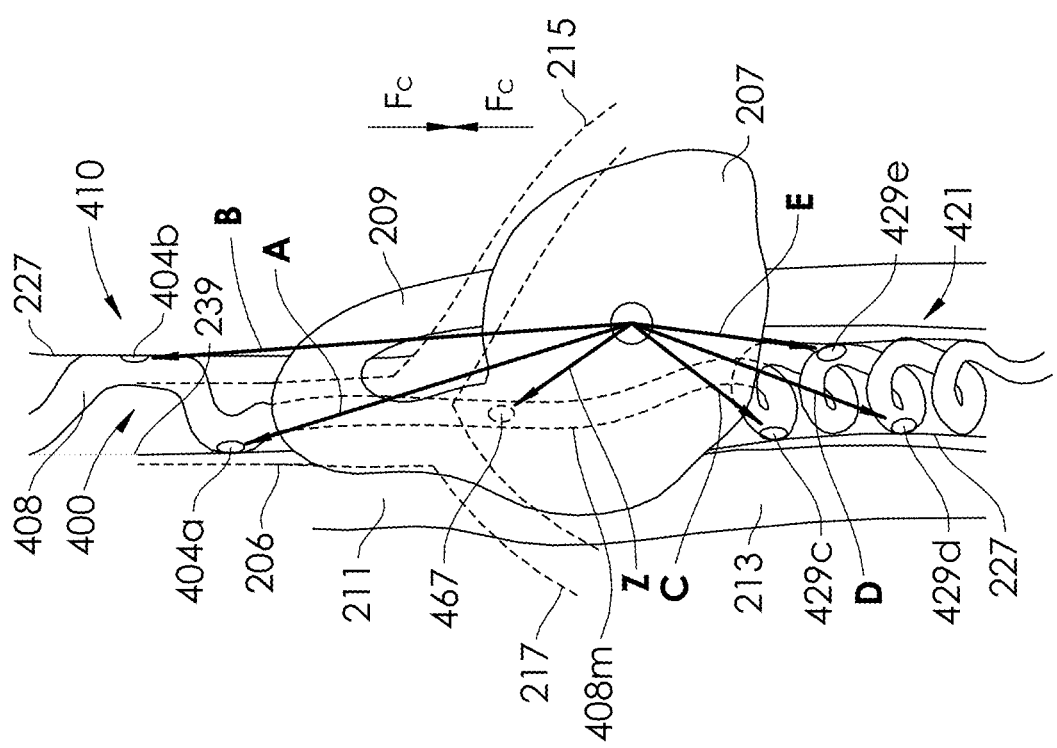
FIG. 15 is a view of a sensing device placed within the esophagus of a subject according to an embodiment of the present disclosure.

Sensing device 400 is shown in FIG. 15 within the esophagus 227 with the first actuation portion 410 and second actuation portion 421 in their expanded states. Sensors 404a, 404b have been forced by the first actuation portion 410 against the interior wall 239 of the esophagus 227 and sensors 429c, 429d, 429e have been forced by the second actuation portion 421 against the interior wall 239 of the esophagus 227. Each of the sensors 404a, 404b, 429c, 429d, 429e are electrodes for leads A, B, C, D, and E, respectively. Vectors A, B, C, D, and E indicate leads A, B, C, D, and E, respectively. For reference purposes the aorta 209, superior vena cava 211, inferior vena cava 213, trachea 206, and two bronchi 215, 217 are illustrated. An additional sensor 467 may be carried on the elongate member 408 of the sensing device 400, on an intermediate portion 408m of the elongate member 408 which is between the first actuation portion 410 and the second actuation portion 421. The intermediate portion 408m is configured so that it may be flexed by applying a compressive force Fc between the first actuation portion 410 and the second actuation portion 421. For example, the user may partially retract the elongate body 457 of the stylet 453 from the second actuation portion 421 and the intermediate portion 408m, to allow only the second actuation portion 421 to change from its low-profile state to its expanded state, and to increase the flexibility of the intermediate portion 408m. With the second actuation portion 421 applying a normal force and accompanying frictional force against the interior wall 239 of the esophagus 227, the user may apply a compressive force Fc by advancing the proximal portion of the elongate member 408, thus flexing the intermediate portion 408m and forcing the sensor 467 against the interior wall 239 of the esophagus 227. While maintaining the compressive force Fc, the user can then retract the elongate body 457 of the stylet 453 from the first actuation portion 410 to allow it to change from its low-profile state to its expanded state. The first actuation portion applies a normal force and accompanying frictional force against the interior wall 239 of the esophagus 227, thus maintaining the intermediate portion 408m in a flexed state and maintaining the sensor 467 against the interior wall 239 of the esophagus 227. The sensor 467 is an electrode for leads Z, with vector Z indicating lead Z. The sensing device 400 is thus configured so that at least one sensor may be positioned superior to the heart, at least one sensor may be positioned within the level of the heart (e.g., within the "footprint" of the heart"), and at least one sensor may be positioned inferior to the heart, all simultaneously. The variance in position between each of these sensors allows for a range of different leads, all with internal electrode (sensor) placement. This may be combined with the variance in location along the diameter of the esophagus to further vary the resulting vectors. By using the markings 437, 439 to adjust the depth of insertion and/or rotational orientation of the sensors 404a, 404b, 467, 429c, 429d, 429e, optimized ECG signals 418 may be obtained.

Figure 16:
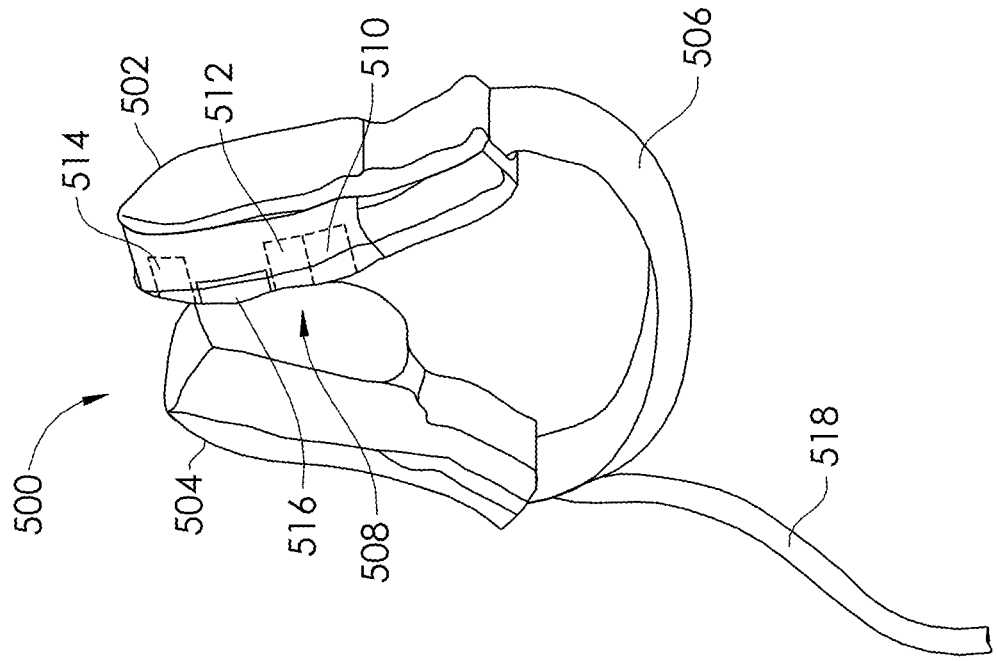
FIG. 16 is an auxiliary sensor according to an embodiment of the present disclosure.

An auxiliary sensor 500 is illustrated in FIG. 16 which is configured for coupling to a variety of soft tissue sites in the body of a subject, including, but not limited to the tongue, soft palate, nostril/nasal passage, cheek, anus, urethra or any other location which allows contact with the subject's mucosa. In some cases, the auxiliary sensor 500 may be applied externally, for example, on the subject's shoulder. The auxiliary sensor 500 comprises first and second heads 502, 504 which are joined by a spring body 506 which produces an increasing bias between the first and second heads 502, 504 as they are moved apart from each other, thus acting similar to a clip. As illustrated in FIG. 16, the first head 502 may include an optical sensor 508 comprising one or more emitters 510, 512 and a one or more detectors 514. The optical sensor 508 can function as a pulse oximetry device to measure oxygen saturation ($SpO_2$). In some embodiments, the optical sensor 508 may be configured to measure peripheral capillary oxygen saturation. The first head 502 also includes a sensor 516 (for example, an electrode) configured to contact soft tissue at an auxiliary site, such as those mentioned. Signals from the optical sensor 508 and sensor 516 are carried via a cable 518 which can connect the auxiliary sensor 500 to any of the consoles 202, 302, 402 described herein. In an alternative embodiment, the optical sensor 508 and the sensor 516 may be carried on opposite heads 502, 504 of the auxiliary sensor 500. In another alternative embodiment, the auxiliary sensor may contain only the sensor 516.

Figures 17, 18:
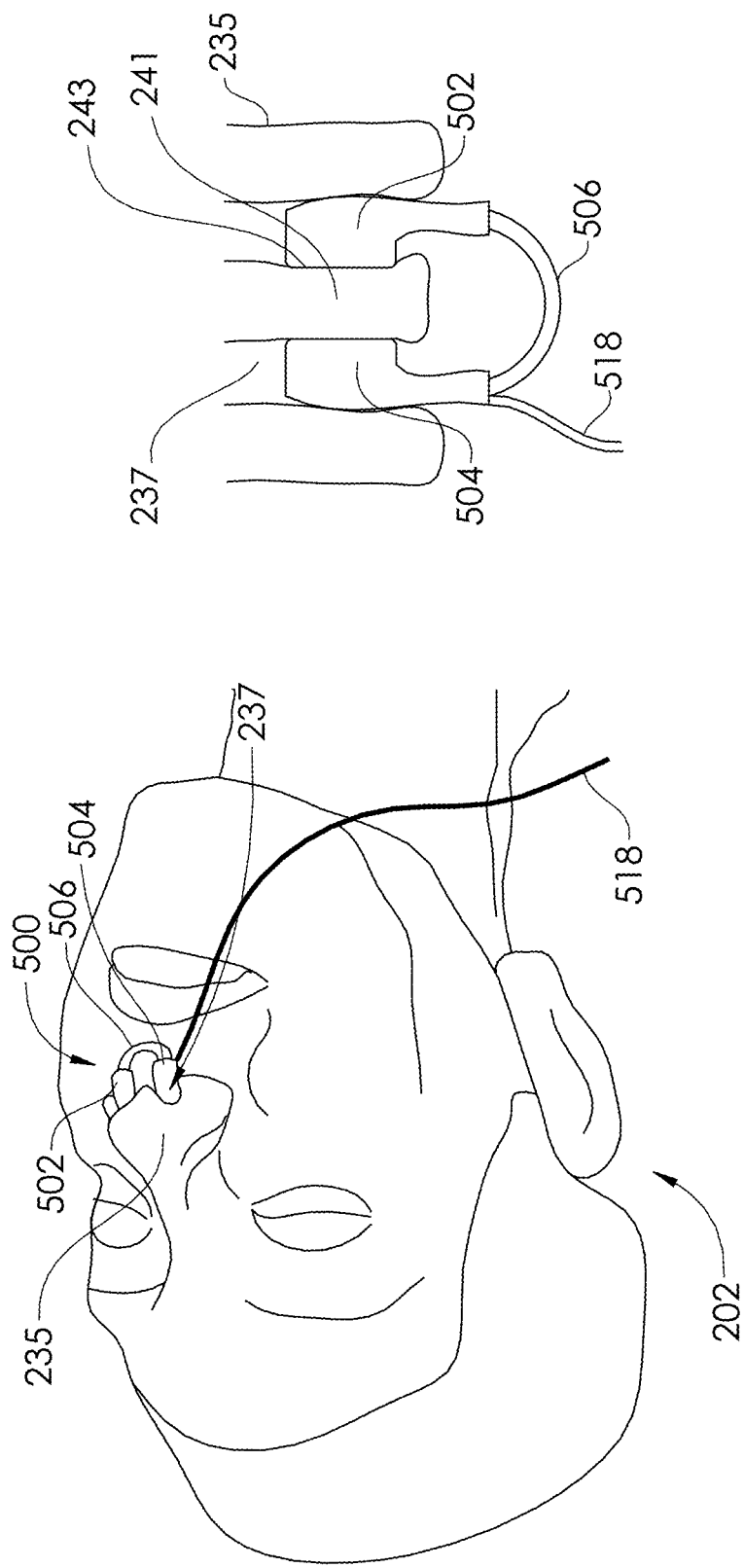
FIG. 17 is a perspective view of a subject having an auxiliary sensor placed on a portion of the nose.
FIG. 18 is a sectional view of the auxiliary sensor in place on the subject's nose.

The auxiliary sensor 500 is shown coupled to a septum 243 of the nose 235 of a patient 202 in FIGS. 17 and 18. The sensors 508, 516 on head 502 are directly adjacent soft tissue 243 of the septum 243. The sensor 516 as an electrode may be coupled to the soft tissue 243 without the use of a coupling gel of liquid. Signals from the sensor 516 may be processed by any of the processors 274, 374, 474 of the consoles 220, 320, 420 of the various systems 20, 30, 40.

Figure 20:
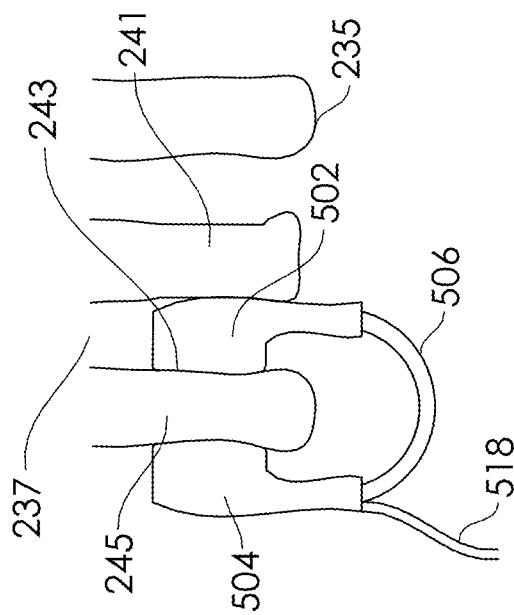
FIG. 20 is a sectional view of the auxiliary sensor in place on the subject's nose.
Figure 19:
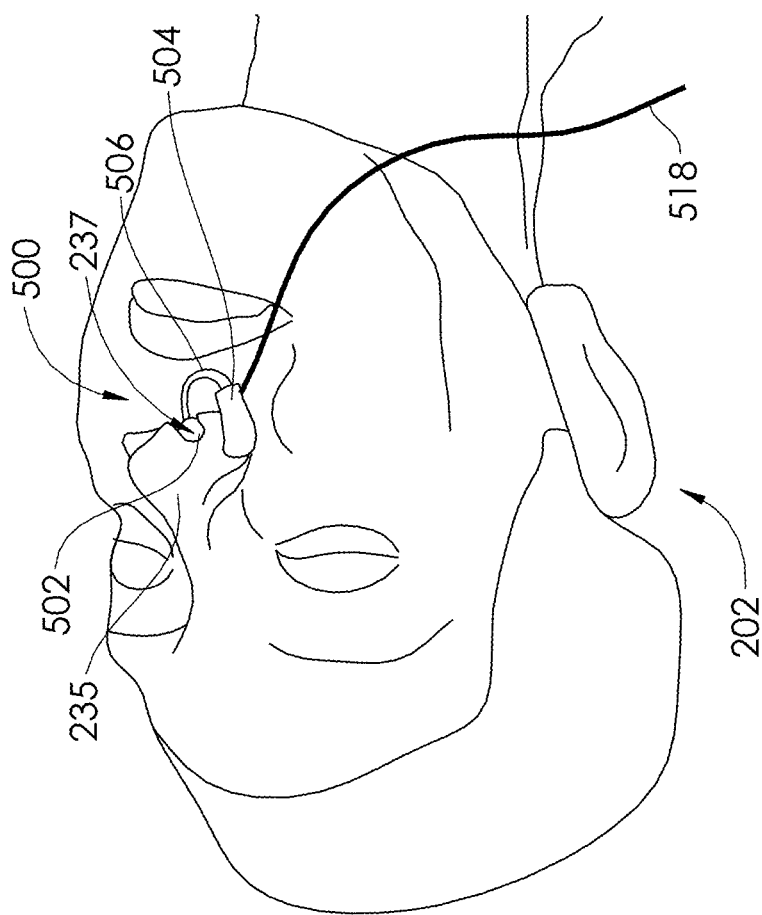
FIG. 19 is a perspective view of a subject having an auxiliary sensor placed on a portion of the nose.

The auxiliary sensor 500 is shown coupled to a nostril wall 245 of the nose 235 of a patient 202 in FIGS. 19 and 20. The sensors 508, 516 on head 502 are directly adjacent soft tissue 243 of the nostril wall 245. The sensor 516 as an electrode may be coupled to the soft tissue 243 without the use of a coupling gel of liquid. Signals from the sensor 516 may be processed by any of the processors 274, 374, 474 of the consoles 220, 320, 420 of the various systems 20, 30, 40.

The auxiliary sensor 500 is shown coupled to the tongue 247 of a patient 202 in FIGS. 21 and 22. The sensors 508, 516 on head 502 are directly adjacent soft tissue 243 of the tongue 247. In some cases, sensors 508, 516 may be placed adjacent the bottom of the tongue 247. The sensor 516 as an electrode may be coupled to the soft tissue 243 without the use of a coupling gel of liquid. Signals from the sensor 516 may be processed by any of the processors 274, 374, 474 of the consoles 220, 320, 420 of the various systems 20, 30, 40.

Figure 24:
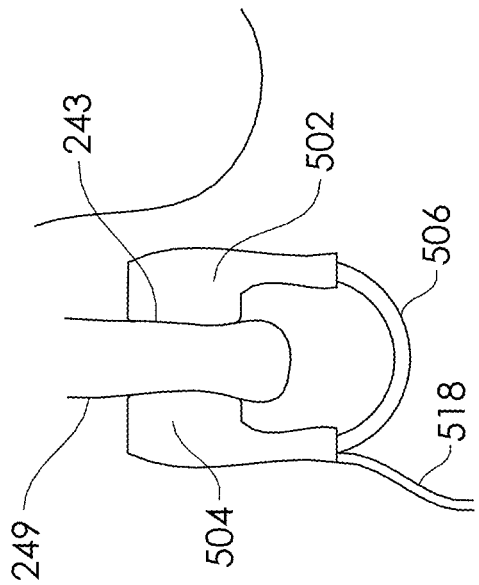
FIG. 24 is a sectional view of the auxiliary sensor in place on the subject's cheek.
Figure 23:
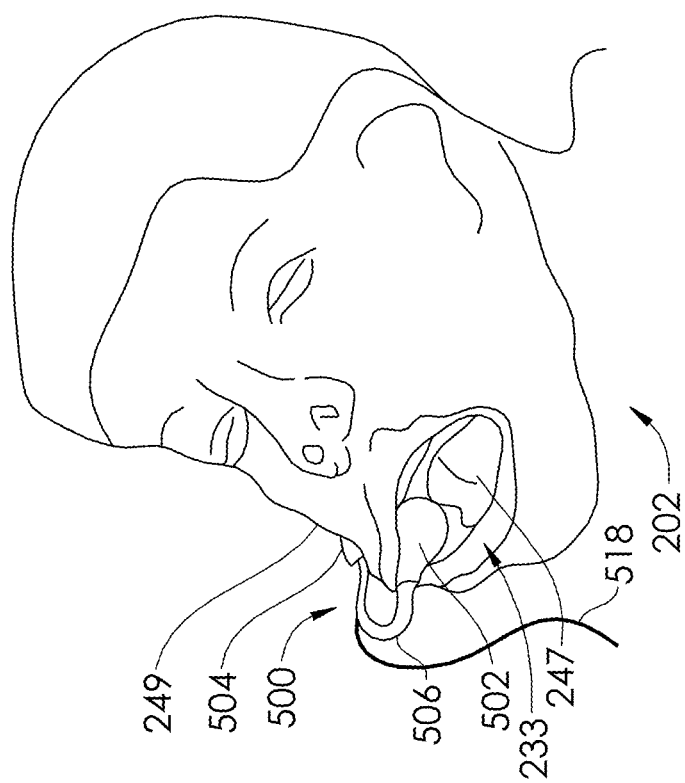
FIG. 23 is a perspective view of a subject having an auxiliary sensor placed on a portion of the cheek.

The auxiliary sensor 500 is shown coupled to the cheek 249 of a patient 202 in FIGS. 23 and 24. The sensors 508, 516 on head 502 are directly adjacent soft tissue 243 of the interior of the cheek 249, within the mouth 233. The sensor 516 as an electrode may be coupled to the soft tissue 243 without the use of a coupling gel of liquid. Signals from the sensor 516 may be processed by any of the processors 274, 374, 474 of the consoles 220, 320, 420 of the various systems 20, 30, 40.

Figure 25:
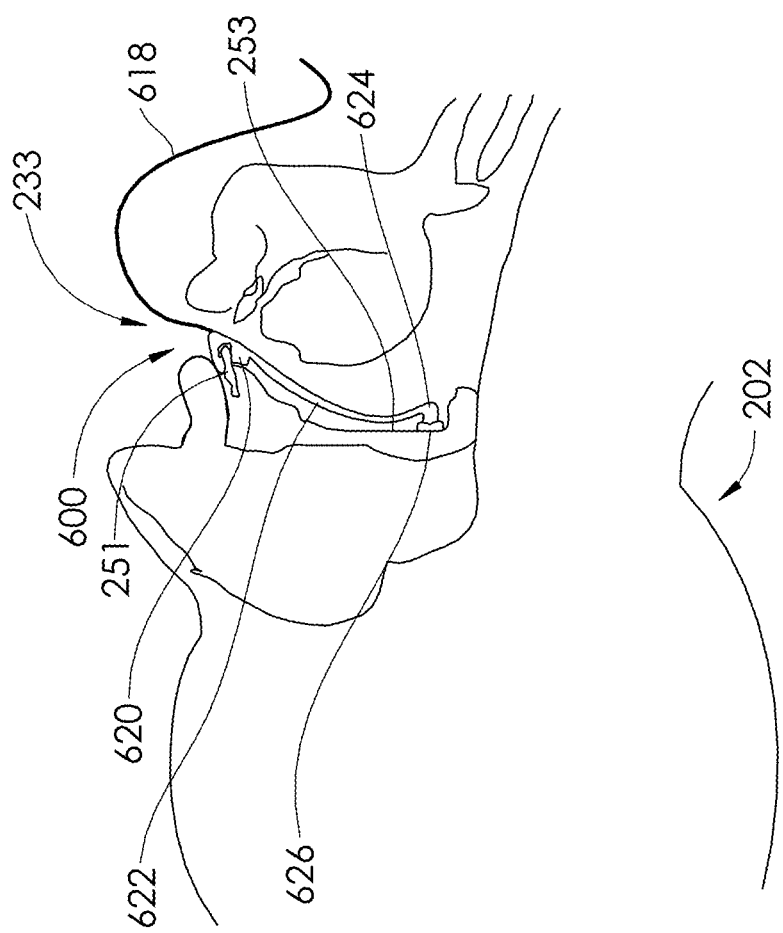
FIG. 25 is a sectional view of a subject having an auxiliary sensor coupled to the subject's soft palate.

Another embodiment of an auxiliary sensor 600 is shown coupled to the soft palate 253 of the mouth 233 of a patient 202 in FIG. 25. The auxiliary sensor comprises a frame 622 having a tooth clip 620 and a base 624. The tooth clip 620 may be snapped onto one or more tooth 251. The base may be structured to apply a bias to force one or more sensors 626 attached to the base 624 directly against the soft palate 253. The one or more sensors 626 include an electrode that can be coupled to the soft palate 253 tissue without the use of a coupling gel of liquid. Signals from the one or more sensors 626 may be delivered through a cable 618 and processed by any of the processors 274, 374, 474 of the consoles 220, 320, 420 of the various systems 20, 30, 40.

Figure 26A:
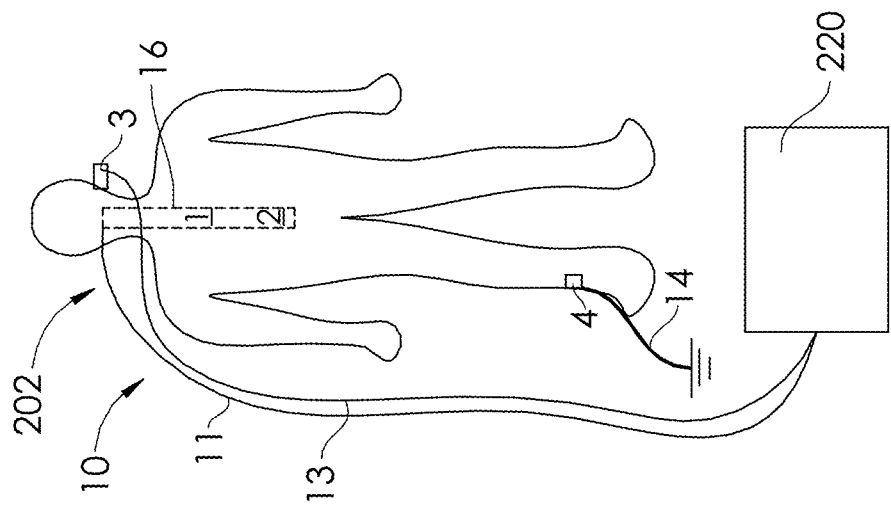
FIG. 26A is a generic flow for a system for sensing electrical activity of the heart according to an embodiment of the present disclosure.

FIG. 26A illustrates generically a sensing system 10 comprising a sensing device 16 which is configured to be coupled to a console 220. The sensing device 16 is configured to be placed internally in the patient 202 and comprises one or more sensors 1, 2 which are used to obtain signals which are delivered to the console on cable 11. An auxiliary sensor 3 is coupled to a portion of the body at a location separate from the sensing device 16. The auxiliary sensor may be an electrode for ECG measurement, but may also be any other type of a sensor whose measurement data can be complimentary to the signals received and/or derived from the sensing device 16. For example, temperature may be sensed by the auxiliary sensor. Cable 13 is configured to carry information from the auxiliary sensor 3 to the console. In some cases, the patient 202 may be grounded via electrode 4 and cable 14. In some embodiments, the auxiliary sensor 3 is packaged with the sensing device 16, and may even share the same cable 11 as the sensing device 16. In some embodiments, two or more electrodes are utilized together to form a bipolar lead.

Figure 26B:
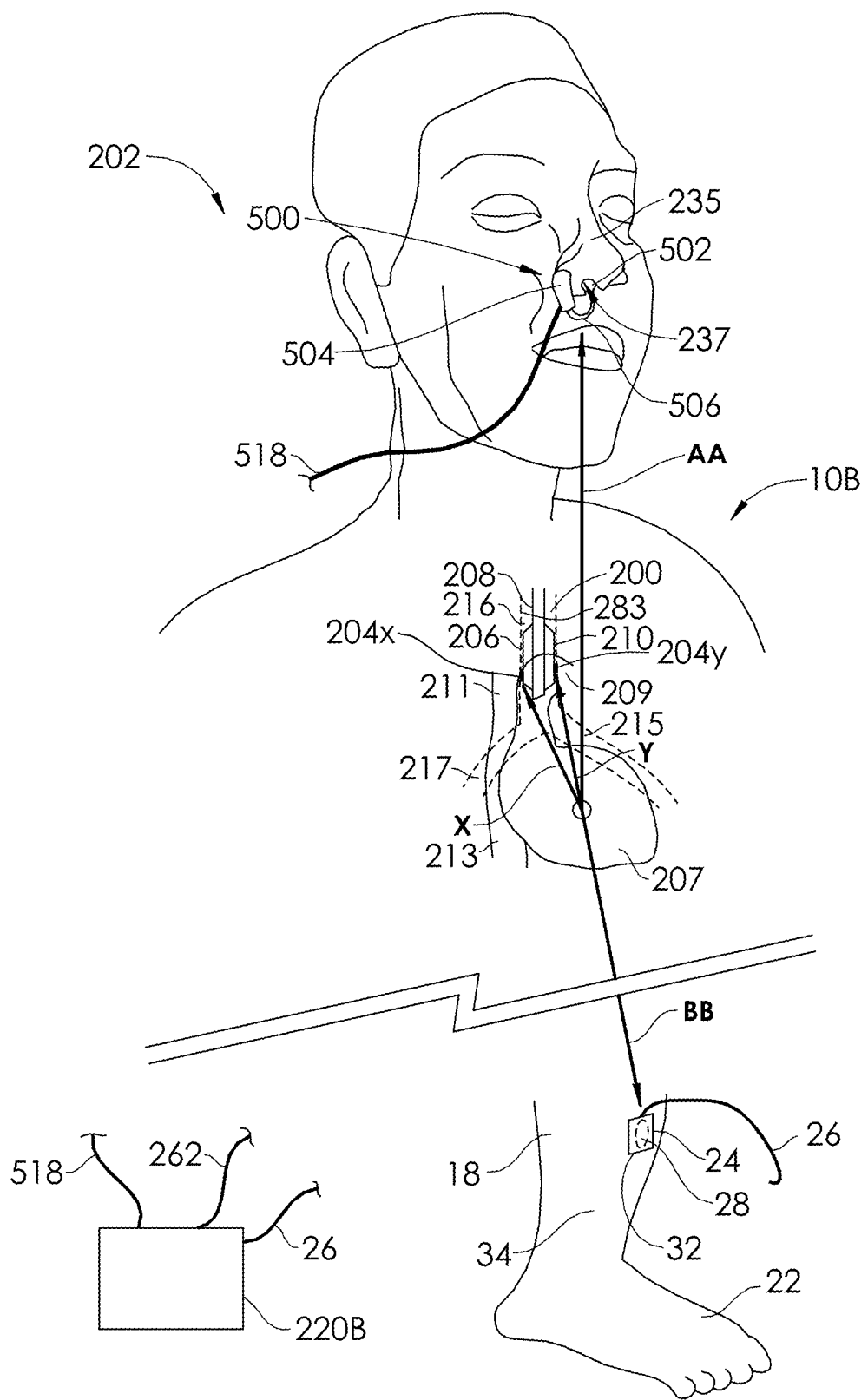
FIG. 26B is a system for sensing electrical activity of the heat according to an embodiment of the present disclosure.

A patient 202 is shown in FIG. 26B with a system 10B for obtaining signals related to electrical activity of the heart, comprising: the sensing device 200 of FIGS. 1 and 7, the auxiliary sensor 500 of FIGS. 16, 19-20, and an external sensor 24 applied to the leg 18 or foot 22 of the patient 202. The sensing device 200 is an endo-tracheal tube having one or more electrodes (sensors 204x, 204y) on its actuation member 210 (inflatable balloon or cuff), and is shown placed within the trachea 206 of the patient 202. The external sensor 24 includes an electrode 28 for application to the skin 34 of the patient 202. The external sensor 24 may also include coupling gel 32 (e.g., a hydrogel or adhesive) or a coupling gel or liquid may be placed between the electrode 28 and the skin 34. A console 220B, similar to the console 220 of FIG. 1, is shown and is configured to connect to the cable 518 of the auxiliary sensor 500, the cable 262 of the sensing device 200, and a cable 26, extending from the external sensor 24, and configured to receive signals from the sensors (e.g., electrodes) of the sensing device 200 (sensors 204x, 204y), the auxiliary sensor 500, and the external sensor 24. The addition of the auxiliary sensor 500 creates an additional lead AA (vector AA). The addition of the external sensor 24 creates an additional lead BB (vector BB). An extended number or portions of the heart and heart muscle, vascular network and nervous tissue can be examined with the combination of these vectors X, Y, AA, BB.

Figure 26C:
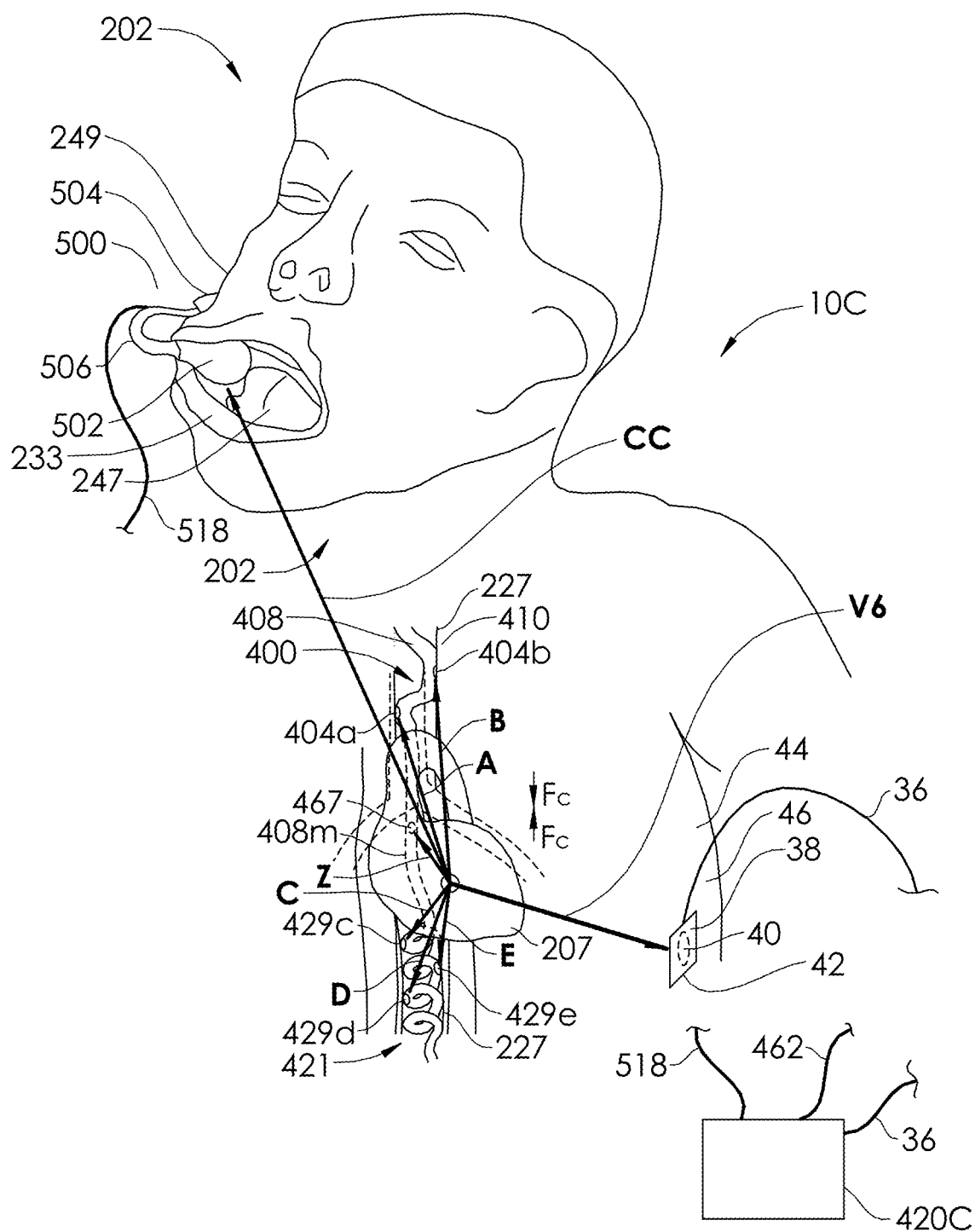
FIG. 26C is a system for sensing electrical activity of the heart according to an embodiment of the present disclosure.

A patient 202 is shown in FIG. 26C with a system 10C for obtaining signals related to electrical activity of the heart, comprising: the sensing device 400 of FIGS. 11 and 15, the auxiliary sensor 500 of FIGS. 16, 23-24, and an external sensor 38 applied to the skin 44 of the chest 46 of the patient 202. The sensing device 400 is a nasogastric (NG) tube having one or more electrodes (sensors 404a, 404b, 467, 429c, 429d, 429e) on its actuation member(s) 410, 408m, 421 (displaceable portions of the elongate member 408), and is shown placed within the esophagus 227 of the patient 202. The external sensor 38 includes an electrode 40 for application to the skin 44 of the patient 202. The external sensor 38 may also include coupling gel 42 (e.g, a hydrogel or adhesive) or a coupling gel or liquid may be placed between the electrode 40 and the skin 44. A console 420C, similar to the console 420 of FIG. 11, is shown and is configured to connect to the cable 518 of the auxiliary sensor 500, the cable 462 of the sensing device 400, and a cable 36, extending from the external sensor 38, and configured to receive signals from the sensors (e.g., electrodes) of the sensing device 400 (404a, 404b, 467, 429c, 429d, 429e), the auxiliary sensor 500, and the external sensor 38. The addition of the auxiliary sensor 500 creates an additional lead CC (vector CC). The addition of the external sensor 38 creates an additional lead V6 (vector V6). Though a common V6 chest ECG lead is shown in FIG. 26C, other chest leads may be used in addition or instead of the V6 lead, such as the V1, V2, V3, V4, or V5, An extended number or portions of the heart and heart muscle, vascular network and nervous tissue can be examined with the combination of these vectors A, B, Z, C, D, E, CC, V6. Other combinations of sensing devices 200, 300, 400 and sensing device locations, with different auxiliary sensor 3, 500 locations and/or external sensor 4, 38, 24 locations, can be created to create a system that obtains desired ECG signals from an array of different vectors.

A process for adding functionality to medical devices made of flexible plastic materials a process was developed to print an electrically conductive flexible electronic circuit on inflatable cuffs, balloons, sleeves or membranes. This process utilizes multidimensional measurement and imaging to establish a specific print pattern program of the device to allow for printing on inconsistent surfaces. Inconsistent surfaces may include folded surfaces, thin surfaces, stretchable surfaces, complex three-dimensional surfaces, uneven surfaces, and even partially or fully overlapping surfaces. The nature of disposable plastic devices that have expandable portions, including those having inflatable portions, is that the dimensions of the surface of the inflatable portions vary due to material inconsistencies, wall thicknesses and inflation pressures. An "intelligent" printing system has been used to adapt to these variations and/or inconsistencies to keep the deposited circuit consistent in dimensions and properties.

As an alternative, an apparatus and method are presented herein for printing and/or depositing and/or applying an electrical circuit using a machine that may be preprogrammed, but which does not require customization of the program for each device. This is accomplished by constraining the inflatable portion within a mask/fixture that has a precisely defined internal diameter. This mask comprises a material that is sufficiently rigid to allow for maintaining that internal diameter when the inflatable material is inflated into contact with the inner surface. The mask may comprise such materials as plastics (Delrin, PEEK, PTFE) or metals (Stainless Steel). The mask has the necessary openings cut out from its surface to allow for a printer or other applicator to deposit/apply the material on the constrained balloon, or inflatable portion, while at a known distance. In some embodiments, the balloon or inflatable portion may be inflated to a desired elevated pressure during the deposition. In some embodiments, this pressure may be adjusted in order to optimize the amount of masking. Alternatively, the "conductive ink" can be (without limitation) sprayed, atomized, painted, sputtered, or vapor deposited on the material exposed by the cut outs to form the circuit. After placement of the conductive tracings, a dielectric layer may be applied over a portion of the conductive tracings, for example, over all except any portions that are to be used as electrodes.

Figures 27, 28:
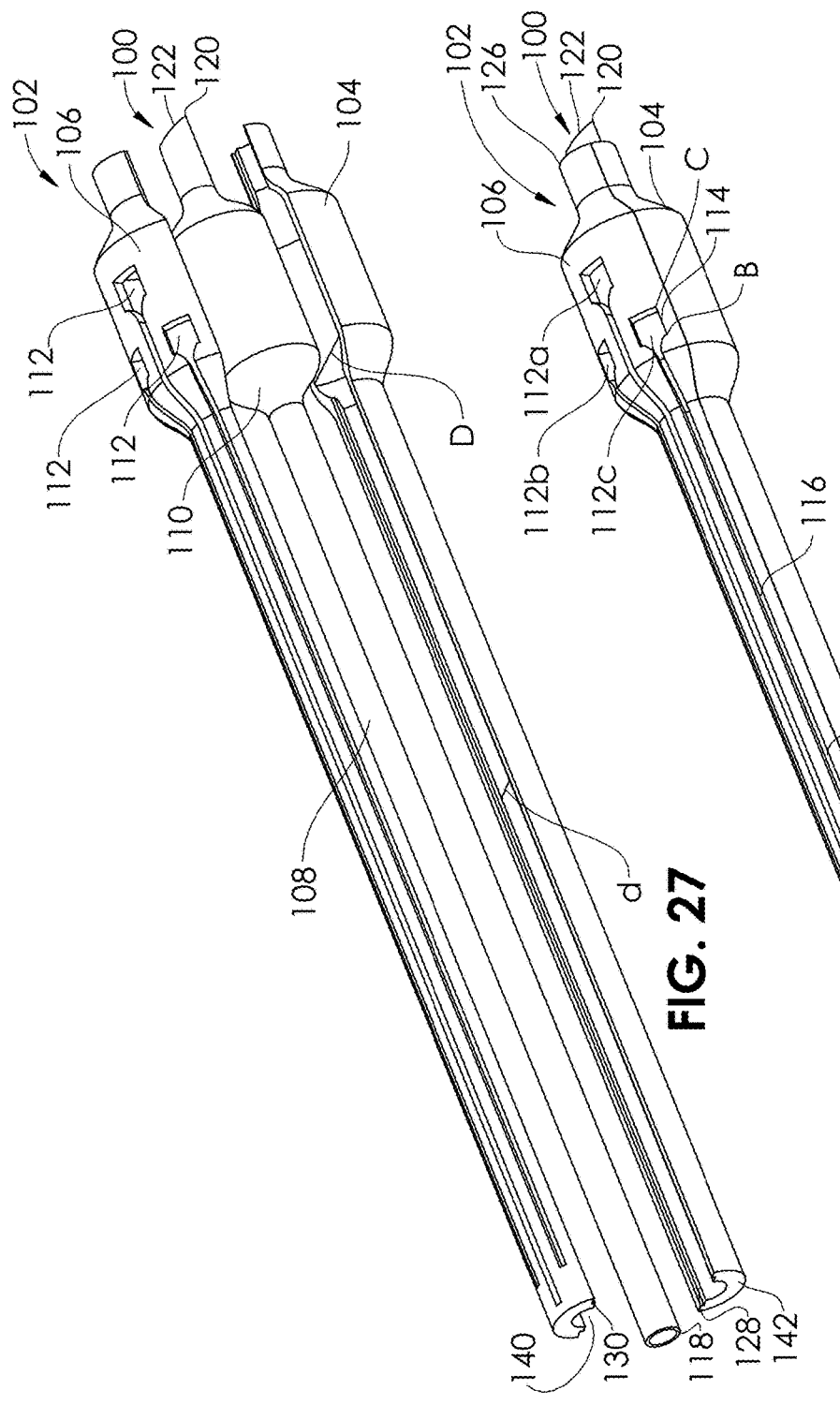
FIG. 27 is a perspective view of an expandable device being placed within a fixture for masking in an open state.
FIG. 28 is a perspective view of an inflatable device in place within a fixture for masking in a closed state, according to an embodiment of the present disclosure.

FIG. 27 illustrates an inflatable device 100 having a shaft 108 and an inflatable portion 110 being placed within a masking fixture 102 (or mask) which comprises a first portion 104 and a second portion 106. The first portion 104 and second portion 106 of the masking fixture 102 may comprise "clamshells," and may include one or more stepped portions 128, 130 for positioning the first portion 104 and second portion 106 relative to one another. The proximal end 118 of the inflatable device 100 may include an inflation port or be bonded to an inflation port. The inflation port may be similar to the interface 212 of FIG. 1, and may be configured to be coupled to an inflation device 250 and a pressure gauge (not shown). The inflatable portion 110 may be inflated to a desired pressure prior to or after the placement of the inflatable device 100 within the masking fixture 102. FIG. 28 illustrates the first portion 104 and second portion 106 of the masking fixture 102 closed on the inflatable device 100. When closed, the masking fixture 102 forms a cavity 140 having first diameter d which closely fits the diameter of the shaft 108, and a second diameter D which closely fits the diameter of the inflatable portion 110 (for example, when the inflatable portion 110 is inflated with an elevated pressure). During the process, the inflatable portion 110 may be inflated with air, nitrogen, carbon dioxide, or a number of other gases. The inflatable portion 110 may alternatively be inflated with an aqueous solution, such as sterile water or pyrogen-free water. The distal end 120 of the inflatable device 100 may include a skive 122, which may, for example, aid in its placement within a body lumen of a patient.

One or both of the first and second portions 104, 106 contains one or more openings 112 which extend completely through the wall 142 of the respective portion 104, 106. The closed masking fixture 102 (FIG. 28) thus covers portions of the inflatable device 100, but leaves a portion of the inflatable device 100 exposed, for controlled application of the conductive material. The proximal end 118 and distal end 120 of the inflatable device 100 are shown extending outside the proximal end 124 and distal end 126 of the masking fixture 102, however, in some embodiments, the masking fixture 102 may completely cover the proximal end 118 and distal end 120 of the inflatable device 100. Multiple openings 112a, 112b, 112c, 112d (not shown), 112e (not shown) may be configured to provide a pattern for a sensor and conductor to be applied to the inflatable portion 110 of the inflatable device 100. As seen in FIG. 28, opening 112c includes an electrode portion 114 and a conductor portion 116, as do each of the other openings 112a, 112b, 112d (not shown), 112e (not shown). The electrode portion 114 may have dimensions on the order of about 5 mm×5 mm square to about 20 mm×20 mm square, or about 10 mm×10 mm square to about 15 mm×15 mm square. The conductor portion 116 may have a transverse width of between about 0.25 mm and about 5 mm, or between about 1 mm and 3 mm.

In use, the inflatable device 100 is placed within the first and second portions 104, 106 of the masking fixture 102 and the first and second portions 104, 106 are secured together (e.g. with clamps, bands, clips, rings). A conductive ink, paint or adhesive is applied to the outside of the openings 112 of the masking fixture 102, and allowed to dry, cure or set. In some embodiments, elevated temperature may be used to activate and/or accelerate the drying, curing, or setting. Prior to the placement of the inflatable device 100 into the masking fixture 102, the inflatable device may be cleaned, dried, abraded, etched, or any other type of surface alteration may be applied, in order to improve the adhesion, adherence or fusion of the conductive ink, paint or adhesive to the inflatable device. Surface treatment may include, but not be limited to, plasma discharge, corona discharge, or bead blasting.

Figure 29:
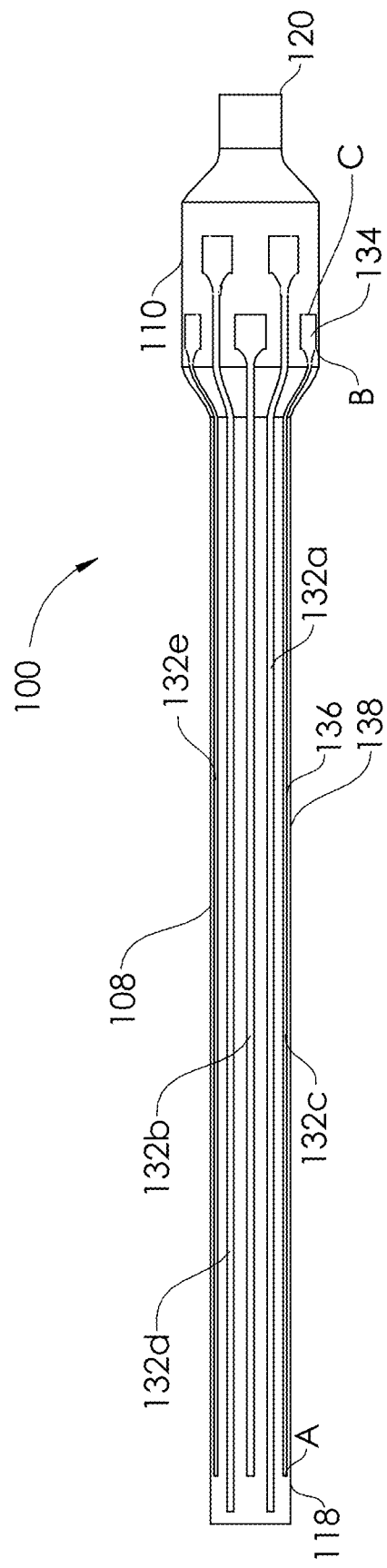
FIG. 29 is an elevation view of an inflatable device with conductive tracings that have been formed with a process utilizing the fixture for masking of FIGS. 27 and 28.

By use of these elements of the process, one or more resulting conductive traces 132 are now secured onto the inflatable device 100, which can be seen in greater detail in FIG. 29. The conductive traces 132a, 132b, 132c, 132d, 132e may each have multiple sections. For example, conductive trace 132c includes an electrode 134 and a conductor 136. Following the step of applying the conductive ink, paint, epoxy, or adhesive to create the conductive traces 132a, 132b, 132c, 132d, 132e, the conductor 136 may have a dielectric layer 138 applied over it, while the electrode 134 is left uncovered. For example, the portion between point A and point B may have a dielectric layer 138 applied over it, while the portion between point B and point C is left uncovered. This can be done with each of the conductive traces 132a, 132b, 132c, 132d, 132e, and may be done while leaving the inflatable device 100 within the masking fixture 102. Alternatively, a separate marking fixture 102 having different patterns for the openings (for example, shorter openings) may be used for applying the dielectric layer 138. Any number of conductive traces 132 may be applied, for example, as many as 100 separate conductive traces 132, each including a sensor and a conductor.

Alternatively, the inflatable device 100 by be removed from the masking fixture 102, and each of the electrodes 134a, b, c, d, e may be temporarily covered by a masking material. The dielectric layer 138 may then be applied over the entire shaft 108, including the conductors 136 (a, b, c, d, e). This may be done by spraying, dipping, painting, deposition (e.g., vapor deposition), etc. After the dielectric layer 138 is applied, the masking material may be removed from the electrodes 134.

Alternatively, the dielectric layer 138 may be applied over the entire surface of the conductive tracings 132, and after setting, may be peeled off and removed only from the portion that includes the electrodes 134.

The masking fixture 102 need not comprise two portions 104, 106, and may instead comprise a single tubular portion. In this case, the inflatable device 100 may be deflated, or even have a vacuum placed on its contents, in order to allow passage of the inflatable device 100 longitudinally through the interior of the masking fixture 102.

Though the exterior of the masking fixture 102 is illustrated with a generally cylindrical shape, the shape may instead be polygonal, for example an octagon. This may aid the application of the conductive material and/or dielectric material, by allowing manual indexing, instead of machine-aided rotational indexing.

Figure 30:
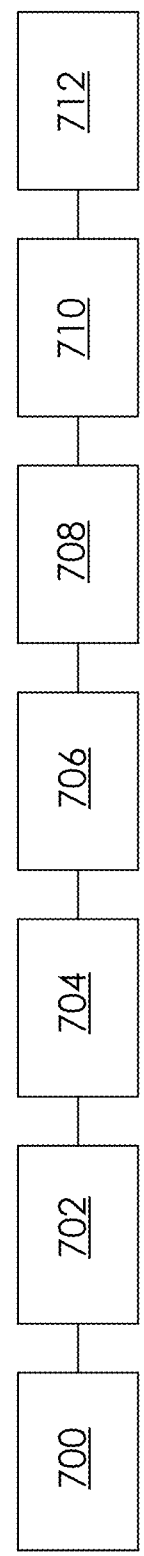
FIG. 30 is a flow chart of a process for forming conductive tracings on an expandable device.

FIG. 30 illustrates a process for forming conductive tracings on a substrate of an expandable device, such as an inflatable balloon or cuff. In operation 700, an inflatable device 100 is placed within a masking fixture 102 having one or more openings 112. In operation 702, a substrate of the masking fixture is treated. This step may be optional, depending on the material being used as the substrate, and may include cleaning, plasma discharge, corona discharge, abrading, or bead blasting. In operation 704, a conductive material is applied on the substrate through the one or more openings 112 in the masking fixture 102. In operation 706, the conductive material is allowed to reach a stable solidified condition to form a tracing 132. In operation 708, a dielectric material is applied over at least a portion of the tracing 132. In operation 710, the dielectric material is allowed to reach a stable solidified condition. In operation 712, the inflatable device is removed from the masking fixture 102. Any device that requires conductive, non-conductive or radiopaque tracings may have these tracings applied by use of the process described in relation to FIG. 30. Devices that may benefit from this process include standard or modified endo-tracheal tubes, nasogastric (NG) tubes, laryngeal masks, gastric lavage tubes, gastric aspiration tubes, gastric decompression tubes, Ewald orogastric tubes, Lavacutor® orogastric tubes, Edlich orogastric tubes, sump tubes, Salem tubes, Levin tubes, gastric suction/feeding tubes, Moss Mark IV nasal tubes, Dobbhoff nasojejunal feeding and gastric decompression tubes, nasointestinal tubes, Miller-Abbott tubes, or Sengstaken-Blakemore tubes, including any of these devices which have any of the embodiments of the sensing devices 200, 300, 400 incorporated therein.

Other embodiments are envisioned which do not incorporate the application of a conductive material, but rather a non-conductive material. Some embodiments may incorporate resistive materials, which may be used to construct a device for delivering thermal therapy to a portion of the body. Some embodiments may incorporate a radiopaque material.

While embodiments have been shown and described, various modifications may be made without departing from the scope of the inventive concepts disclosed herein.

What is claimed is:

1. A method for applying a conductive tracing to an inflatable device, the method comprising:
    placing an inflatable device within a masking fixture having a cavity extending longitudinally therein and a wall, the masking fixture comprising a first portion and a second portion separate from the first portion, the first portion and the second portion configured to be engaged together to form the cavity, the inflatable device comprising an elongate shaft having a proximal end, a distal end, and a shaft diameter, an inflatable portion carried by the distal end of the elongate shaft and having an inflated diameter and a proximal taper when the inflatable portion is in an inflated state, the proximal taper decreasing in diameter from a distal end of the proximal taper at the inflated diameter to a proximal end of the proximal taper adjacent the distal end of the elongate shaft, wherein mask is configured such that the proximal end of the elongate shaft may extend outside of the mask when the inflatable device is placed within the cavity of the masking fixture, the masking fixture including two or more longitudinally extending openings through the wall and into the cavity such that the inflatable device placed within the cavity is partially covered by the wall and partially uncovered by the two or more openings, wherein the two or more openings are separated from each other, wherein the cavity at a first section of the masking fixture has a first diameter, and wherein the cavity at a second section of the masking fixture has a second diameter, smaller than the first diameter, the first diameter configured to closely fit the inflated diameter of the inflatable portion of the inflatable device when inflated, the second diameter configured to closely fit the shaft diameter, and wherein the two or more longitudinally extending openings each extend along at least a portion of the first section of the masking fixture, through a third section between the first section and the second section, and along a portion of the second section of the masking fixture, such that a first of the two or more longitudinally extending openings provides a first uncovered portion of the inflatable device and a second of the two or more longitudinally extending openings provides a second uncovered portion of the inflatable device, the first and second uncovered portions each continuously and smoothly transitioning between the inflated diameter and the shaft diameter;
    applying a conductive material to the first and second uncovered portions of the inflatable device at the first and second of the two or more longitudinally extending openings such that it creates a continuous layer along the inflatable portion, the proximal taper and the elongate shaft; and
    when the continuous layer of conductive material is in a condition that will not significantly change upon removal of the inflatable device from the masking fixture, removing the inflatable device from the masking fixture, such that the inflatable device includes separate first and second conductive traces formed thereon, wherein each of the first and second conductive traces is located at a different rotational orientation than the other of the first and second conductive traces.

2. The method of claim 1, wherein the two or more openings each comprise an electrode portion and a conductor portion.

3. The method of claim 2, wherein the electrode portion is configured to be placed adjacent the inflatable portion of the inflatable device and wherein the conductor portion is configured to be placed adjacent the elongate shaft of the inflatable device.

4. The method of claim 3, further comprising inflating the inflatable portion of the inflatable device to a desired pressure.

5. The method of claim 2, wherein each electrode portion of the two or more openings is between about 25 mm$^2$ and about 400 mm$^2$ in dimension.

6. The method of claim 2, wherein each electrode portion of the two or more openings is between about 100 mm$^2$ and about 225 mm$^2$ in dimension.

7. The method of claim 2, wherein each conductor portion of the two or more openings has a transverse width of between about 0.25 mm and about 5 mm.

8. The method of claim 2, wherein each conductor portion of the two or more openings has a transverse width of between about 1 mm and 3 mm.

9. The method of claim 1, further comprising applying a dielectric material to at least a portion of the first and second conductive traces, after the applying a conductive material step.

10. The method of claim 1, further comprising the step of altering at least some of a surface of the inflatable device prior to the applying a conductive material step.

11. The method of claim 10, wherein the step of altering at least some of the surface comprises at least one of the methods in the list consisting of cleaning, drying, abrading, etching, treating with plasma discharge, treating with corona discharge, and bead blasting.

12. The method of claim 1, wherein the applying a conductive material step comprises applying a conductive ink comprising silver.

13. The method of claim 1, further comprising the step of subjecting the conductive material to UV or visible light radiation after the applying a conductive material step.

14. The method of claim 1, further comprising the step of subjecting the conductive material to an elevated temperature after the applying a conductive material step.

15. The method of claim 1, further comprising the step of rotationally indexing the masking fixture.

16. The method of claim 1, wherein the applying a conductive material step comprises using a programmable machine.

17. The method of claim 1, wherein the inflatable device is selected from the list consisting of an endo-tracheal tube, a nasogastric tube, and a laryngeal mask.

18. The method of claim 17, wherein the inflatable device is configured to obtain signals related to the functioning of the heart of a subject.

19. The method of claim 18, wherein the inflatable device is configured to obtain signals related to the electrical activity of the heart of the subject.

20. The method of claim 1, wherein the first portion of the masking fixture includes one or more of the two or more longitudinally extending openings, and wherein the second portion of the masking fixture includes one or more of the two or more longitudinally extending openings.

21. The method of claim 1, wherein the first portion of the masking fixture is configured to engage a first side of the inflatable device, and wherein the second portion of the masking fixture is configured to engage a second side of the inflatable device, the second side generally opposite the first side.

22. The method of claim 1, wherein the first portion and the second portion are configured to engage each other in a clamshell manner.

* * * * *